United States Patent
Ikemoto et al.

(10) Patent No.: US 9,604,979 B2
(45) Date of Patent: Mar. 28, 2017

(54) PYRROLOQUINOLINE QUINONE ALCOHOL ADDUCT

(71) Applicant: Mitsubishi Gas Chemical Company, Inc., Chiyoda-ku (JP)

(72) Inventors: Kazuto Ikemoto, Niigata (JP); Hitoshi Sakamoto, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 14/349,228

(22) PCT Filed: Sep. 24, 2012

(86) PCT No.: PCT/JP2012/074411
§ 371 (c)(1),
(2) Date: Apr. 2, 2014

(87) PCT Pub. No.: WO2013/051414
PCT Pub. Date: Apr. 11, 2013

(65) Prior Publication Data
US 2015/0037308 A1  Feb. 5, 2015

(30) Foreign Application Priority Data

Oct. 3, 2011  (JP) .................................. 2011-218968

(51) Int. Cl.
| | | |
|---|---|---|
| *A61K 38/43* | (2006.01) | |
| *C07D 471/04* | (2006.01) | |
| *A61K 8/49* | (2006.01) | |
| *A61Q 19/08* | (2006.01) | |
| *A23L 2/52* | (2006.01) | |
| *A23L 2/58* | (2006.01) | |
| *A61K 31/122* | (2006.01) | |
| *A61Q 1/06* | (2006.01) | |
| *A61Q 1/10* | (2006.01) | |
| *A61Q 5/02* | (2006.01) | |
| *A61Q 19/00* | (2006.01) | |
| *A61K 31/4745* | (2006.01) | |

(52) U.S. Cl.
CPC .......... *C07D 471/04* (2013.01); *A23K 20/137* (2016.05); *A23L 2/52* (2013.01); *A23L 2/58* (2013.01); *A23L 5/47* (2016.08); *A23L 33/10* (2016.08); *A61K 8/4926* (2013.01); *A61K 31/122* (2013.01); *A61K 31/4745* (2013.01); *A61Q 1/06* (2013.01); *A61Q 1/10* (2013.01); *A61Q 5/02* (2013.01); *A61Q 19/007* (2013.01); *A61Q 19/08* (2013.01); *A23V 2002/00* (2013.01); *A61K 2800/42* (2013.01)

(58) Field of Classification Search
None
See application file for complete search history.

(56) References Cited

U.S. PATENT DOCUMENTS

| | | | |
|---|---|---|---|
| 8,198,290 B2 | 6/2012 | Hodges | |
| 2007/0101509 A1* | 5/2007 | Huffer | C14C 3/16 |
| | | | 8/94.15 |
| 2011/0152526 A1 | 6/2011 | Hodges | |

FOREIGN PATENT DOCUMENTS

| | | | |
|---|---|---|---|
| JP | 05-070459 A | 3/1993 | |
| JP | 2011-024476 A | 2/2011 | |
| JP | 2011148755 A | * | 8/2011 |

OTHER PUBLICATIONS machine translation of JP 2011148755 downloaded from the JPO Nov. 8, 2016.*
International Search Report issued Nov. 6, 2012 in PCT/JP2012/074411 (with English language translation).

(Continued)

Primary Examiner — Susan Hanley
(74) Attorney, Agent, or Firm — Oblon, McClelland, Maier & Neustadt, L.L.P.

(57) ABSTRACT

The present invention relates to a compound represented by the formula (A) or (B), or a salt thereof capable of improving a red color of pyrroloquinoline quinone (PQQ) and obtaining functions of original PQQ, and to a method of efficiently manufacturing the compound.

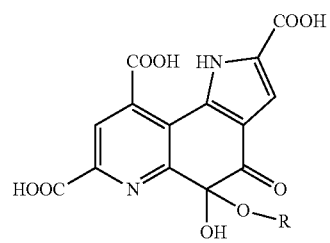

(A)

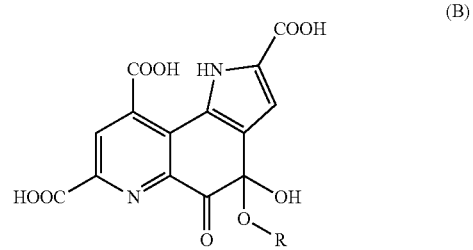

(B)

wherein R is an alkyl group, a hydroxyalkyl group, a dihydroxyalkyl group, or an alkoxyalkyl group.

19 Claims, 15 Drawing Sheets

(56) References Cited

OTHER PUBLICATIONS

International Preliminary Report on Patentability and Written Opinion issued Apr. 8, 2014 in PCT/JP2012/074411 (submitting English translation only).

Robert H. Dekker, et al., "Covalent addition of H2O, enzyme substrates and activators to pyrrolo-quinoline quinone, the coenzyme of quinoproteins", European Journal of Biochemistry, vol. 125, No. 1, 1982, pp. 69-73.

Johannes Frank Jzn, et al., "Kinetic and spectral studies on the redox forms of methanol dehydrogenase from Hyphomicrobium X", European Journal of Biochemistry, vol. 174, No. 2, 1988, pp. 331-338.

J. Andrés, et al., "Quantum chemical studies of pyrroloquinoline quinone: PM3 pathways of methanol oxidation", Bioorganic Chemistry, vol. 22, No. 1, Mar. 1994, pp. 58-71.

Shinobu Itoh, et al., "C-4 and C-5 adducts of cofactor PQQ (pyrroloquinolinequinone). Model studies directed toward the action of quinoprotein methanol dehydrogenase", Journal of the American Chemical Society, vol. 115, No. 22, 1993, pp. 9960-9967.

Michael C. Pirrung, "Modeling of the chemistry of quinoprotein methanol dehydrogenase. Oxidation of methanol by calcium complex of coenzyme PQQ via addition-elimination mechanism", Chemtracts-Organic Chemistry, vol. 10, No. 11, Oct. 1997, pp. 828-830.

Shizuka Saito, et al., "Quinone hemiacetal formation from protocatechuic acid during the DPPH radical scavenging reaction", Bioscience, Biotechnology, and Biochemistry, vol. 67, No. 7, Aug. 8, 2003, pp. 1578-1579.

Shinobu Itoh, et al., "Reaction of reduced PQQ (PQQH$_2$) and molecular oxygen", Bulletin of the Chemical Society of Japan, vol. 59, 1986, pp. 1911-1914.

Johannis A. Duine, et al., "Structure and activity of the prosthetic group of methanol dehydrogenase", European Journal of Biochemistry, vol. 108, 1980, pp. 187-192.

Aya Ouchi, et al., "Kinetic study of the antioxidant activity of pyrroloquinolinequinol (PQQH$_2$, a reduced form of pyrroloquinolinequinone) in micellar solution", Journal of Agricultural and Food Chemistry, vol. 57, No. 2, 2009, pp. 450-456.

E.J. Corey, et al., "Total synthesis of the quinonoid alcohol dehydrogenase coenzyme (1) of methylotrophic bacteria", Journal of the American Chemical Society, vol. 103, 1981, pp. 5599-5600.

\* cited by examiner

PYRROLOQUINOLINE QUINONE ALCOHOL ADDUCT

CROSS-REFERENCE TO RELATED APPLICATIONS

This application is a National Stage of PCT/JP2012/074411 filed on Sep. 24, 2012. This application is based upon and the claims the benefit of priority to Japanese Application No. 2011-218968 filed on Oct. 3, 2011.

BACKGROUND OF THE INVENTION

Technical Field

The present invention relates to a novel derivative of pyrroloquinoline quinone represented by the following formula (1).

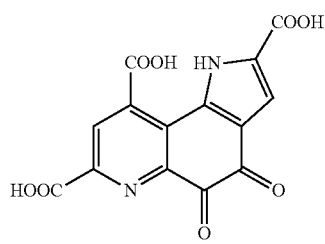

(1)

Background Art

Pyrroloquinoline quinone (hereinafter, also referred to as "PQQ") has been suggested to have a possibility of a new vitamin, and has been attracted as a substance useful for health supplements and cosmetics. Moreover, PQQ exists in not only bacteria but eukaryotes such as fungus and yeast, and performs important functions as a coenzyme. Furthermore, until recent years, PQQ had been clarified to have many physiological activities such as a cell growth promotion effect, an anticataract effect, a liver disorder preventive care effect, a wound healing effect, an anti-allergic effect, a reverse-transcriptase inhibiting effect, and a glyoxalase I inhibiting effect-anticancer effect.

This PQQ has an absorption in a visible part. Therefore, a free body and an alkali metal salt of PQQ are a solid or a solution having a color between red and dark red (for example, refer to Non Patent Document 1, 2, and 3).

As a PQQ derivative, for example, an esterified derivative obtained by reacting a carboxylic acid in PQQ with an alcohol has been reported (for example, refer to Non Patent Document 2 and 4).

On the other hand, a composition containing PQQ and an alcohol has been reported so far (for example, refer to Patent Document 1). In addition, as a reaction product of PQQ and an alcohol, a carboxylic acid ester of PQQ and a hemiacetal form to which an alcohol is further added have been reported (for example, refer to Non Patent Document 5).

LIST OF PRIOR ART DOCUMENTS

Patent Document

Patent Document 1: Japanese Patent Laid-Open No. 2011-24476

Non Patent Document

Non Patent Document 1: Bull. Chem. Soc. Jpn., vol. 59, p. 1911-1914 (1986)

Non Patent Document 2: Eur. J. Biochem., 108, 187-192 (1980)

Non Patent Document 3: J. Agric. Food Chem. 2009, 57, 450-456

Non Patent Document 4: J. Am. Chem. Soc., 1981, 103, 5599-5600

Non Patent Document 5: J. Am. Chem. Soc., 1993, 115, 9960-9967

SUMMARY OF INVENTION

Problems to be Solved by Invention

Recently, PQQ has been attempted to be contained in foods and cosmetics because it has many physiological activities as described above. However, since the free body and the alkali metal salt of PQQ described in Non Patent Document 1 to 3 have the color between red and dark red, a preference may be decreased by making them be directly contained in foods and cosmetics. Therefore, in the case where the free body of PQQ and the salt thereof (for example, alkali metal salt) are made to be contained in foods and cosmetics, they are required to be changed to a mild color other than red color while maintaining functions of PQQ in consideration of the high preference of foods and cosmetics.

Examples of a method for changing the color of the free body of PQQ and the salt thereof include a coating method and a mixing method. However, these methods need to make a new component be mixed so as to change the color, and a disadvantage is that the degree of freedom of component design of foods, cosmetics, drugs and the like using PQQ is decreased.

Furthermore, examples of the method for changing the color of the free body of PQQ and the salt thereof include a method for changing a chemical structure. For example, since the chemical structure of the esterified PQQ derivative described in Non Patent Document 2 and 4 is changed from original PQQ, it is considered that an absorption wavelength (color) is also changed. It is considered that such an esterified PQQ derivative is hydrolyzed with relative ease to return to the original PQQ, but in fact, the hydrolysis rate thereof is slow and it is difficult to return to the original PQQ. Moreover, similarly, it is also difficult for the carboxylic acid ester of PQQ and the hemiacetal form thereof described in Non Patent Document 5 to return to the original PQQ. Thus, the method for changing a chemical structure can change the color, but it is difficult to obtain functions of the original PQQ because of large change in physical properties.

On the other hand, the composition containing PQQ and an alcohol described in Patent Document 1 is just a composition, and is not a reaction product of PQQ and an alcohol.

Furthermore, it is known that PQQ exerts functions by being mixed particularly with coenzyme Q10. Since coenzyme Q10 is a yellow solid, it is dappled when being mixed with PQQ having a color between red and dark red, and appearance becomes worse. Therefore, a method for suppressing change in a color hue even if PQQ and coenzyme Q10 are mixed is desired.

Therefore, it is a subject of the present invention to provide a novel compound capable of improving the red color of PQQ and obtaining functions of the original PQQ, and a method of efficiently manufacturing the compound.

Means for Solving Problems

The present inventors have made extensive research so as to solve the above-described subject, and have found that it can be solved by the following items.
[1] A compound represented by the following formula (A) or (B), or a salt thereof:

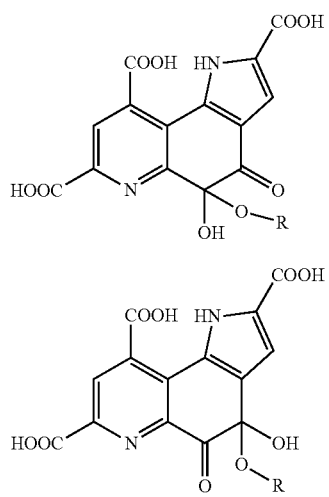

wherein R is an alkyl group, a hydroxyalkyl group, a dihydroxyalkyl group, or an alkoxyalkyl group.
[2] A composition comprising the compound or the salt thereof according to [1].
[3] The composition according to [2], further comprising coenzyme Q10.
[4] Beverages comprising the compound or the salt thereof according to [1], or the composition according to [2] or [3].
[5] Foods comprising the compound or the salt thereof according to [1], or the composition according to [2] or [3].
[6] Cosmetics comprising the compound or the salt thereof according to [1], or the composition according to [2] or [3].
[7] The composition according to [2] or [3], wherein the composition is in a form of a powder, a tablet, a chewable tablet, a capsule, a granule, an injectable, a liquid, an eye drop, a lotion, a hair tonic, a cosmetic emulsion, a spray liquid, an aerosol, a drink liquid, a liquid fertilizer, or a preservation solution.
[8] A method for manufacturing the compound or the salt thereof according to [1], comprising a step of adding one equivalent of an alcohol represented by the following formula (2) to pyrroloquinoline quinone represented by the following formula (1) or a salt thereof:

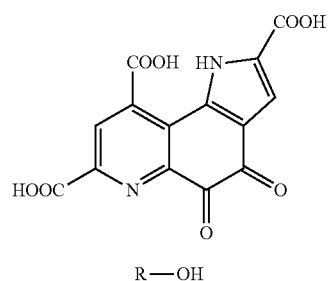

wherein R is an alkyl group, a hydroxyalkyl group, a dihydroxyalkyl group, or an alkoxyalkyl group.
[9] The method according to [8], wherein the step is performed in a solvent having a water content of 50 mass % or less.
[10] The method according to [8] or [9], wherein the salt of pyrroloquinoline quinone is a monoalkali metal salt.

Advantages of Invention

According to the present invention, a novel compound having a color between pale yellow and orange and functions of original PQQ can be provided, and furthermore, a method of efficiently manufacturing the compound can be provided.

MODE FOR CARRYING OUT INVENTION

Figure 1:
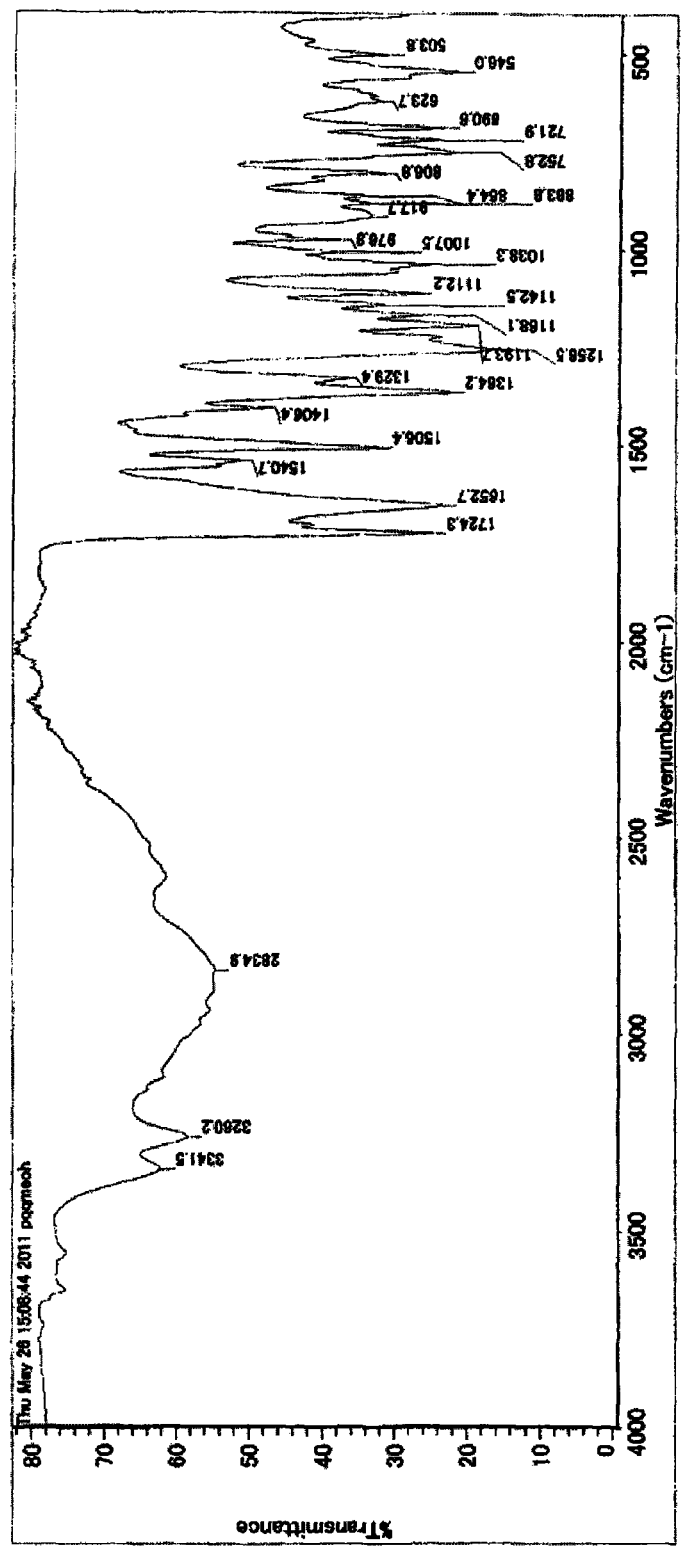
FIG. 1 is a diagram showing an IR result of a PQQ methanol adduct.

Hereinafter, an embodiment of the present invention (hereinafter, also referred to as "present embodiment") will be described in detail. It is to be noted that the following embodiment is an example for explaining the present invention and the present invention is not limited to only the embodiment.

The present embodiment is a compound represented by the following formula (A) or (B), or a salt thereof.

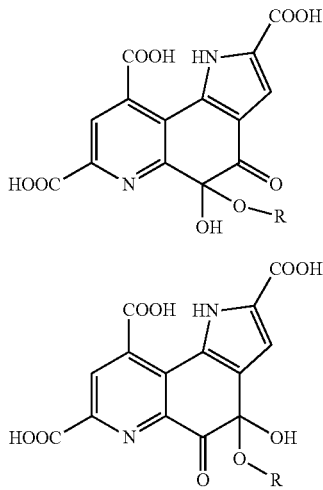

In the above formulas (A) and (B), R is an alkyl group, a hydroxyalkyl group, a dihydroxyalkyl group, or an alkoxyalkyl group.

In the above formulas (A) and (B), R is preferably a methyl group, an ethyl group, a propyl group, a hydroxyethyl group, a hydroxypropyl group, and a dihydroxypropyl group, more preferably an ethyl group, a methyl group, a propyl group, a hydroxypropyl group, and a dihydroxypropyl group, and further preferably an ethyl group.

The compound or the salt thereof in the present embodiment can be obtained, for example, by adding one equivalent of an alcohol represented by the following formula (2) (hereinafter, also referred to as "alcohol") with respect to pyrroloquinoline quinone represented by the following formula (1) (hereinafter, also referred to as "PQQ" or "PQQ free body") or a salt thereof.

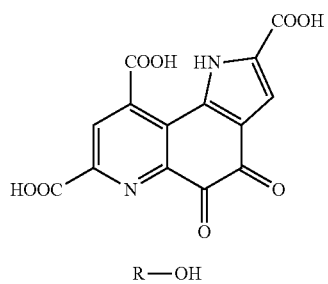

(In the formula (2), R is an alkyl group, a hydroxyalkyl group, a dihydroxyalkyl group, or an alkoxyalkyl group.)

Although not particularly limited, examples of the salt of PQQ represented by the above formula (1) include a mono, di, or trialkali metal salt of PQQ, and a mono, di, or triammonium salt of PQQ. More specifically, examples thereof include a monosodium salt of PQQ, a disodium salt of PQQ, a trisodium salt of PQQ, a monopotassium salt of PQQ, a dipotassium salt of PQQ, a tripotassium salt of PQQ, a monolithium salt of PQQ, a dilithium salt of PQQ, a trilithium salt of PQQ, a monoammonium salt of PQQ, a diammonium salt of PQQ, and a triammonium salt of PQQ.

The above PQQ or the salt thereof used in the present embodiment is preferably a free body of PQQ, a monoalkali metal salt of PQQ, or a monoammonium salt of PQQ, and particularly preferably a free body of PQQ, a monosodium salt of PQQ, a monopotassium salt of PQQ, and a monolithium salt of PQQ, which are easily available.

In the above formula (2), R is preferably an alkyl group, a hydroxyalkyl group, a dihydroxyalkyl group, or an alkoxyalkyl group having a carbon number of 1 to 700. However, it does not contain a primary amino group.

The molecular weight of the alcohol represented by the above formula (2) is preferably 30 to 10000, and more preferably 32 to 1000. When the molecular weight of the alcohol represented by the above formula (2) is within the above range, the reactivity with respect to PQQ represented by the above formula (1) or the salt thereof tends to become better.

In addition, specific examples of the alcohol represented by the above formula (2) preferably include primary or secondary alcohols. The primary or secondary alcohols have less steric hindrance and can rapidly undergo an addition reaction with respect to PQQ represented by the above formula (1) or the salt thereof. In particular, as described below, when the alcohol represented by the above formula (2) is a primary alcohol, for example, PQQ to which the alcohol is added is easy to dissociate the added alcohol in water, and thus, functions of the original PQQ free body can be easily obtained.

Although not particularly limited, specific examples of the alcohol represented by the above formula (2) include methanol, ethanol, propanol, butanol, hexanol, octanol, dodecanol, ethylene glycol, propylene glycol, glycerin, ethylene glycol monoethyl ether, ethylene glycol monobutyl ether, diethylene glycol monomethyl ether, diethylene glycol monoethyl ether, diethylene glycol monobutyl ether, propylene glycol monomethyl ether, propylene glycol monoethyl ether, propylene glycol monobutyl ether, dipropylene glycol monomethyl ether, dipropylene glycol monoethyl ether, diethylene glycol monobutyl ether, diethylene glycol, dipropylene glycol, and polyethylene glycol. In particular, the alcohol represented by the above formula (2) is preferably methanol, ethanol, propanol, propylene glycol, ethylene glycol, and glycerin, more preferably methanol, propanol, ethanol, propylene glycol, and glycerin, and further preferably ethanol.

The compound represented by the following formula (A) or (B), or the salt thereof in the present embodiment is, for example, a compound or a salt thereof (hereinafter, also referred to as "PQQ alcohol adduct") obtained by adding one equivalent of the alcohol of the above formula (2) with respect to PQQ represented by the above formula (1) or the salt thereof.

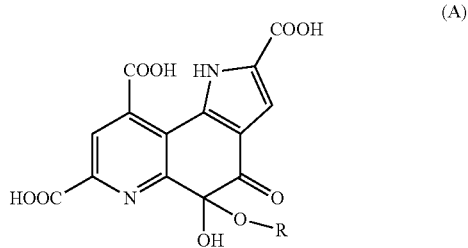

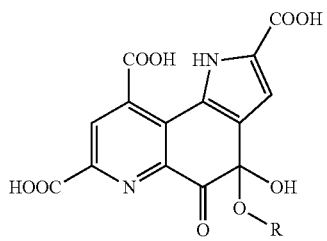

(B)

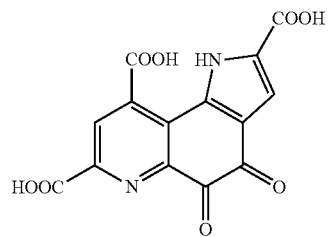

(1)

(2)
R—OH (In the formulas (A) and (B), R is an alkyl group, a hydroxyalkyl group, a dihydroxyalkyl group, or an alkoxyalkyl group.)

The PQQ alcohol adduct of the present embodiment has the advantage of being capable of changing physical properties of PQQ without requiring particular reagents and catalysts. The solid or the liquid of the original PQQ has a red color, whereas the PQQ alcohol adduct of the present embodiment becomes the solid or the liquid having a color between pale yellow and yellow by adding the alcohol to PQQ. Since the conjugated system in PQQ is cut by adding the alcohol to PQQ, the PQQ alcohol adduct of the present embodiment appears to be a yellowish color for the human eye. Therefore, if a color other than red is required, the PQQ alcohol adduct of the present embodiment is easy to be used for, in particular, applications in foods and cosmetics having a high preference.

In addition, when being mixed with coenzyme Q10, the color of the PQQ alcohol adduct of the present embodiment is less likely to be dappled because it is similar to the color of coenzyme Q10.

The PQQ alcohol adduct of the present embodiment is easy to dissociate the alcohol and returns to the original PQQ in water, and thus, the same functions as PQQ can be obtained in the case of oral administration or the like. In particular, the PQQ alcohol adduct of the present embodiment is easy to dissociate the added alcohol and return to the original PQQ in a water solution containing 80 mass % or more of water. Furthermore, the added alcohol is preferably primary because the PQQ alcohol adduct of the present embodiment is easy to dissociate the alcohol.

Although all functions of alcohols cannot be described as functions of an arbitrary alcohol, in the case of low-molecular ethanol or methanol, it has a bactericidal property, and thus, examples of the functions include a function of decreasing the risk that a substance is contaminated by the bacteria.

Moreover, for example, by using an alcohol having large steric hindrance as the alcohol to be added, the PQQ alcohol adduct of the present embodiment can decrease a dissociation property of the alcohol and can also change solubility into a solvent, absorbability into cells, and the like.

Next, a method of manufacturing the PQQ alcohol adduct of the present embodiment will be described in detail.

The method of manufacturing the PQQ alcohol adduct of the present embodiment comprises a step of adding one equivalent of an alcohol represented by the following formula (2) to PQQ represented by the following formula (1) or a salt thereof.

(R is an alkyl group, a hydroxyalkyl group, a dihydroxyalkyl group, or an alkoxyalkyl group.)

In the above step, the PQQ free body or the salt thereof may be a solid, or a solution by being dissolved in a solvent.

As the PQQ free body, the PQQ free body can be directly used, whereas the PQQ free body generated by making the salt of PQQ acidic in the solution can also be used. When the free body is generated from the salt of PQQ, although pH in the solution varies depending on a solvent and a salt to be mixed, it is preferably 2 or less in the case of a general water solution. The generated PQQ free body can be used by being dried and separated.

Although not particularly limited, examples of the salt of PQQ used in the manufacturing method of the present embodiment include a mono, di, or trialkali metal salt of PQQ, and a mono, di, or triammonium salt of PQQ. More specifically, examples thereof include a monosodium salt of PQQ, a disodium salt of PQQ, a trisodium salt of PQQ, a monopotassium salt of PQQ, a dipotassium salt of PQQ, a tripotassium salt of PQQ, a monolithium salt of PQQ, a dilithium salt of PQQ, a trilithium salt of PQQ, a monoammonium salt of PQQ, a diammonium salt of PQQ, and a triammonium salt of PQQ. A dialkali metal salt of PQQ is preferable, and a disodium salt of PQQ or a dipotassium salt of PQQ is more preferable.

Preferably, a di or trialkali metal salt of PQQ, or a di or triammonium salt of PQQ is treated by a reaction with acid to be used as a free body of PQQ, a monoalkali metal salt of PQQ, or a monoammonium salt of PQQ. In particular, in the manufacturing method of the present embodiment, the salt of PQQ is preferably a monoalkali metal salt.

In the above step, in the case where an alkali metal salt of PQQ is used as the salt of PQQ, preferably, an acid which forms a salt with an alkali metal, for example, hydrochloric acid, sulfuric acid, phosphoric acid, nitric acid, citric acid, tartaric acid, acetic acid or the like, is added, and after removing water and the like, one equivalent of the alcohol represented by the above formula (2) is added.

In the above step, in the case of using a solvent, the same alcohol as the alcohol to be added to PQQ may be used as the solvent. That is, the alcohol to be added is preferably used as a solvent. In the case of using a solvent different from the alcohol to be added, a solvent which does not react with PQQ is preferable as the solvent, and examples thereof include an aprotic polar solvent. The aprotic polar solvent is easy to be used because of good solubility with respect to PQQ. In the above step, in the case of using a solvent, the amount of the solvent used is preferably within the range of 0.5 mL to 1000 L with respect to 1 g of PQQ.

The above step is preferably performed in a solvent having the water content of 50 mass % or less. The water content in the solvent is more preferably 20 mass % or less, and further preferably 10 mass % or less. When the water content in the solvent is within the above range, discoloration of PQQ tends to successfully proceed, and furthermore, a formed hemiacetal structure is difficult to be fractured and return to the original PQQ structure. It is to be noted that, in the water-rich condition such as in a living organism, the PQQ alcohol adduct returns to the original PQQ free body to exert the same functions as the PQQ free body.

In the above step, the PQQ free body or the salt thereof is preferably brought into contact with the alcohol at 0° C. to 200° C. Accordingly, the PQQ free body or the salt thereof can be efficiently discolored from the red color to the yellow color. The contact temperature between the PQQ free body or the salt thereof and the alcohol is more preferably 20° C. to 150° C., and further preferably 30° C. to 120° C. When the contact temperature between the PQQ free body or the salt thereof and the alcohol is within the above range, discoloration of PQQ successfully proceeds, and change of properties of PQQ can also be suppressed.

In the above step, the contact time between the PQQ free body or the salt thereof and the alcohol may be, for example, about 30 seconds to 1 week, although it varies depending on conditions such as the temperature and the used alcohol. In the above step, in the case of using methanol or ethanol as the alcohol, the PQQ alcohol adduct can be generated in a few minutes even at room temperature because of high reactivity of methanol or ethanol. That is, the PQQ alcohol adduct is generated at the same time as the PQQ free body or the salt thereof is diluted and mixed with the alcohol as the solvent. On the other hand, in the case of using an alcohol which is bulky and has large steric hindrance in the above step, in order to efficiently generate the PQQ alcohol adduct, preferably, the contact temperature between the PQQ free body or the salt thereof and the alcohol is increased and the contact time therebetween is lengthened.

In the above step, the alcohol is preferably brought into contact with the PQQ free body or the salt thereof in the liquid or gas state, and is more preferably brought into contact with the PQQ free body or the salt thereof in the liquid state.

In the above step, the blending ratio (molar ratio) of the PQQ free body or the salt thereof and the alcohol may be an excess of the alcohol. The blending ratio (PQQ free body or salt thereof:alcohol) is more preferably 1:10 to 100000. One equivalent of the alcohol can be added to PQQ or the salt thereof by such a blending ratio.

In the above step, the PQQ alcohol adduct generated by the contact of the PQQ free body or the salt thereof and the alcohol may be isolated, or can be used for various applications described below even in the coexisting state with the unreacted alcohol.

In the case where the PQQ alcohol adduct is precipitated as a solid, examples of a method for isolating the PQQ alcohol adduct include a method for performing recrystallization using a solvent. When the PQQ alcohol adduct is stable, separating methods such as chromatography can also be used.

The specific method of manufacturing the PQQ alcohol adduct of the present embodiment will be described. As the typical example, the method of manufacturing a PQQ ethanol adduct will be described.

Firstly, a disodium salt of PQQ is dissolved in water to obtain a water solution. By adding hydrochloric acid to the water solution, pH is made to be 0 to 2, and a red solid is precipitated. The precipitated red solid is collected by filtration, washed with 2N or less of hydrochloric acid, washed with water and isopropanol, and then dried under reduced pressure to obtain the PQQ free body.

The obtained PQQ free body is heated in an ethanol solvent at a temperature equal to or less than the boiling point of ethanol so that ethanol is added to the PQQ free body. When heating at a temperature equal to or more than the boiling point of ethanol, it is preferably performed in a pressure vessel. The solution is discolored from the red color to the yellow color as the addition reaction proceeds, and a yellow solid is precipitated. The precipitated yellow solid is isolated by centrifugation or filtration. The isolated yellow solid is dried by air or dried under reduced pressure so that a pale yellow solid can be obtained. The pale yellow solid is the PQQ ethanol adduct.

Although not particularly limited, examples of preservation methods of the PQQ alcohol adduct of the present embodiment include low-temperature preservation, anaerobic preservation by an airtight container, and light-shielding preservation. In addition, the PQQ alcohol adduct of the present embodiment may be brought into a solution by being dissolved in a solvent to be preserved by the above-described methods. According to the above-described methods, the PQQ alcohol adduct can be stably preserved without generating a precipitate.

A composition of the present embodiment contains the above-described PQQ alcohol adduct. One kind of the PQQ alcohol adduct may be used alone, or two kinds or more of the PQQ alcohol adduct may be used in combination.

In addition, the composition of the present embodiment may further contain the original PQQ, coenzyme Q10, vitamins such as ascorbic acid, and other food components, and in particular, preferably further contains coenzyme Q10. Coenzyme Q10 may be reduced or oxidized coenzyme Q10, and oxidized coenzyme Q10 is preferable.

Furthermore, the composition of the present embodiment is preferably in the form of a powder, a tablet, a chewable tablet, a capsule, a granule, an injectable, a liquid, an eye drop, a lotion, a hair tonic, a cosmetic emulsion, a spray liquid, an aerosol, a drink liquid, a liquid fertilizer, or a preservation solution.

In the present embodiment, for example, PQQ may be used alone as food and changed to the PQQ alcohol adduct by being brought into contact with an alcohol to discolor, or PQQ may be changed to the PQQ alcohol adduct by being brought into contact with an alcohol after being mixed into other foods to discolor.

The composition of the present embodiment may be in the form of a powder or a solution. In the case where the composition of the present embodiment is a mixture of the above-described PQQ alcohol adduct and other components, any method may be applied, for example, mixing with other components may be performed in the powdered state, they may be mixed in the solution state and the solvent is removed to obtain a solid, or components in the powdered state and components in the solution state may be mixed.

The compound or the salt thereof of the present embodiment, or the composition of the present embodiment can be extensively used in, for example, medical drugs, quasi drugs, cosmetics, beverages, foods (also referred to as "foods and beverages" as the combination of beverages and foods), functional foods, feeding stuffs, and garden supplies. Among them, the compound or the salt thereof of the present embodiment, or the composition of the present embodiment is preferably used in beverages, foods, or cosmetics.

The foods and beverages, functional foods, and feeding stuffs containing the compound or the salt thereof of the present embodiment, or the composition of the present embodiment express effects based on physiological action of PQQ, for example, effects such as cell growth promotion, liver disorder preventive care, suppression of melanin production, and promotion of nerve growth factor production. Therefore, the beverages, foods, functional foods, and feeding stuffs containing the compound or the salt thereof of the present embodiment, or the composition of the present embodiment are suitable for health foods, functional foods and beverages, foods and beverages for specified health use, foods and beverages for patients, or feeding stuffs, pet foods and the like for domestic animals, racehorses, ornamental animals or the like which attempt these effects and indicate the effects.

The foods and beverages, functional foods, feeding stuffs, and garden supplies containing the compound or the salt thereof of the present embodiment, or the composition of the present embodiment can be manufactured according to a conventional method by blending other materials used for manufacturing foods and beverages, functional foods, feeding stuffs, and garden supplies, for example, various nutrients, various vitamins, minerals, amino acids, various fats and oils, various additives (for example, taste components, sweeteners, acidulants such as organic acids, preservatives, thickening agents, coloring agents, bleaching agents, antibacterial and antifungal agents, surfactants, pH adjusters, stabilizers, antioxidizing agents, pigments, and flavors) and the like. Alternatively, the functional foods, foods and beverages, feeding stuffs, and garden supplies of the present embodiment can be manufactured by blending the composition of the present embodiment into commonly consumed foods and beverages, functional foods, feeding stuffs, and garden supplies.

The forms of the foods and beverages, functional foods, feeding stuffs, and garden supplies are not particularly limited and can be, for example, powdery, solid, semi-solid, or liquid, or examples thereof include various forms such as tablets, chewable tablets, powder materials, capsules, granules, drinks, gels, syrups, and liquid foods for tube enteral nutrition.

Specific forms of the foods and beverages are not particularly limited, and examples thereof include tea drinks such as green tea, oolong tea, and black tea, drinks such as coffee drink, soft drink, jelly drink, sport drink, milk drink, carbonated drink, fruit juice drink, lactic fermented milk drink, fermented milk drink, powder drink, cocoa drink, alcoholic drink, and purified water, miso, soy sauce, instant miso soup, Chinese noodle, pan-fried noodle, curry, corn soup, mapo tofu, mapo eggplant, pasta sauce, pudding, cake, spreads such as butter, jam, dried seasoning powder, and margarine, mayonnaise, shortening, custard cream, dressings, breads, rices, noodles, pasta, miso soup, tofu, milk, yoghurt, soups or sauces, and confectionery (for example, biscuits or cookies, chocolate, candy, cake, ice cream, chewing gum, and tablet). The feeding stuffs of the present embodiment can be used in the same constituent and form as those of the foods and beverages and functional foods.

The medical drugs or quasi drugs may contain pharmaceutically acceptable carriers. The carriers are not particularly limited, and examples thereof include excipients, coatings, binders, extenders, disintegrants, lubricants, diluents, surfactants, osmotic adjusters, pH adjusters, dispersants, emulsifiers, preservatives, stabilizers, antioxidizing agents, wetters, thickeners, injectables, alcohols, waters, water-soluble polymers, and colorants, fragrances, flavoring agents, odor improving agents and the like which add colors, fragrances, and flavors to formulations. These carriers can be appropriately used alone or in arbitrary combination depending on the formulation type of the medical drugs or quasi drugs.

The formulation type when being used for the medical drugs or quasi drugs is preferably the formulation type of oral or dermal administration. The formulation type for oral formulations is not particularly limited, and examples thereof include tablets, capsules, granules, powders, syrups, dry syrups, liquids, and suspensions. Examples of the formulation type for dermal formulations are not particularly limited, and include lotions, gels, creams, sprays, ointments, patches, and plasters.

In the case of formulating as oral drugs, for example, additives such as excipients, binders, disintegrants, lubricants, dispersants, suspending agents, emulsifiers, diluents, buffers, antioxidants, and antibacterial agents can be used.

The formulation type when being used for the cosmetics is not particularly limited as long as it is a formulation type used for normal cosmetics, and examples thereof include ointments, creams, emulsions, lotions, powders, masks, bath salts, shampoos, rinses, hair treatments, lipsticks, eyeliners, spray liquids, and hair tonics. The cosmetics can be manufactured by the same method as normal cosmetics, except that the composition of the present embodiment is blended.

EXAMPLES

Hereinafter, the present invention will be described in more detail with reference to examples and comparative examples, but the present invention is not limited to only these examples and comparative examples.

[Raw Materials]

PQQ disodium manufactured by Mitsubishi Gas Chemical Company, Inc. was used. Reagents manufactured by Wako Pure Chemical Industries, Ltd. were used for those which are not particularly specified.

[Various Analysis Methods]

(UV Measurement)

The UV measurement of the PQQ alcohol adduct or the like was performed using U-2000 spectrometer manufactured by HITACHI, Ltd.

(High-Performance Liquid Chromatography Analysis)

The high-performance liquid chromatography analysis of the PQQ alcohol adduct or the like was performed as follows.

A column: YMC-Pack ODS-TMS (5 μm) 150×4.6 mm I.D. was arranged in a high-performance liquid chromatography LC-20A manufactured by Shimadzu Corporation, and detection was performed at 260 nm using an eluent of 100 mM $CH_3COOH$/100 mM $CH_3COONH_4$ (30/70, pH 5.1) and an absorption detector.

(Nuclear Magnetic Resonance (NMR))

The nuclear magnetic resonance (NMR) measurement of the PQQ alcohol adduct or the like was performed using 500 MHz NMR, JNM-ECA500 spectrum meter manufactured by JEOL Ltd.

(FT-IR Measurement)

The FT-IR measurement of the PQQ alcohol adduct or the like was performed by ATR (Dia) using Thermo Scientific NICOLET6700.

Example 1

Methanol Adduct

Thirty-seven wt % of concentrated hydrochloric acid was added to 3 g/L of a PQQ disodium water solution to make pH of the water solution be 2 or less, and a red PQQ free body was precipitated. The precipitated PQQ free body was collected by filtration, and dried under reduced pressure to obtain PQQ free body powder. 0.25 g of the obtained PQQ free body powder and 40 g of methanol were mixed to be reacted at 65° C. for 5 hours. The reaction liquid was charged in an eggplant flask and a solvent was removed by an evaporator to obtain 0.28 g of a yellow solid in which a small amount of a red solid is mixed. The obtained solid was further washed with 6 mL of methanol to obtain 0.28 g of a pale yellow solid (PQQ methanol adduct).

Example 2

Reaction with Methanol 1.5 g of the PQQ free body obtained in the same manner as Example 1 and 39 g of methanol were mixed and charged in a glass bottle. The glass bottle was put into an ultrasonic washer and an ultrasonic wave is applied for 1 hour so that the mixture in the bottle was changed from the red color to the yellow color. The yellow mixture was separated by a centrifugal machine to obtain 3.48 g of a solid. The obtained solid was left in the atmosphere for drying to obtain 1.40 g of a pale yellow solid (PQQ methanol adduct).

Example 3

Reaction with Gas Methanol 30 mg of the PQQ free body obtained in the same manner as Example 1 was brought into contact with 8.5 g of methanol vapor at 66° C. for 30 minutes so that the PQQ free body that is a red solid was made to change into a yellow solid. 33 mg of the yellow solid (PQQ methanol adduct) was obtained. Accordingly, it was found that the reaction of the PQQ free body with an alcohol proceeds even if a gaseous alcohol is used.

Example 4

LC Analysis

The PQQ methanol adduct obtained in Example 1 was added to a phosphate buffer (manufactured by Invitrogen pH 7.4) to obtain 1 mg/ML of a PQQ methanol adduct solution. After the PQQ methanol adduct solution was left at room temperature for 2 hours, the high-performance liquid chromatography analysis was performed. According to the analysis, it was found that 0.92 mg/ML of PQQ exists in the PQQ methanol adduct solution. That is, the PQQ methanol adduct obtained in Example 1 returned to the original PQQ free body by the addition of the phosphate buffer and being left at room temperature for 2 hours.

Example 5

Ethanol Adduct 1.98 g of the PQQ free body obtained in the same manner as Example 1 and 40 g of ethanol were mixed to be reacted at 65° C. for 6 hours to precipitate a yellow solid. The precipitated yellow solid was centrifuged, washed with ethanol, and dried under reduced pressure to isolate 1.95 g of a pale yellow solid (PQQ ethanol adduct).

Example 6

Methoxyethanol Adduct 15 g of methoxyethanol and 380 mg of the PQQ free body obtained in the same manner as Example 1 were mixed to be reacted at 60° C. for 16 hours, and then left at room temperature for 3 days to precipitate a yellow solid. The precipitated yellow solid was centrifuged, washed with diethyl ether, and dried under reduced pressure to isolate 0.28 g of a yellow solid (PQQ methoxyethanol adduct).

Example 7

NMR, IR Analysis

The PQQ methanol adduct and the PQQ ethanol adduct obtained in Examples 2 and 5 were analyzed as follows.
1) Measurement in Deuterated Methanol ($CD_3OD$) Solvent In deuterated methanol, $^1$H-NMR, $^{13}$C-NMR, and 2D measurement such as HMBC and HMQC of the PQQ methanol adduct obtained in Example 2 were performed.

According to the result of $^1$H-NMR of the PQQ methanol adduct obtained in Example 2 in deuterated methanol, the obtained chemical shifts (integral ratio) were 3.30 s (3), 7.31 s (1), and 8.77 s (1) ppm. It was found that, from the result, one molecule of methanol is added to the PQQ methanol adduct obtained in Example 2. When the methanol which undergoes the addition reaction was changed to deuterated methanol to form a deuterated methanol adduct and the measurement was performed in the same manner, a peak derived from the methyl group was not observed.

According to the result of $^{13}$C-NMR of the PQQ methanol adduct obtained in Example 2 in deuterated methanol, there were peaks at 49.23, 114.24, 122.91, 124.52, 128.66, 129.09, 135.04, 136.75, 145.75, 160.15, 162.68, 166.89, 170.11, 185.28, and 188.08 ppm. The peak at 49.23 ppm was a peak derived from the solvent, and it was found that, from the 2D measurement, it was a peak of the added methyl group.

Accordingly, the chemical shift of the peak was not contradictory to the hemiacetal structure represented by the following formula (4).

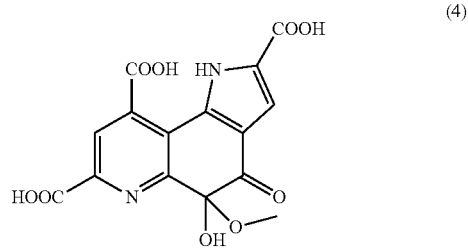 [SMILES: COC1(O)C(=O)c2cc(C(=O)O)[nH]c2-c2c(C(=O)O)cc(C(=O)O)nc21]

(4)

Furthermore, $^1$H-$^1$H COSY and NOESY measurement was performed for structure determination of the PQQ methanol adduct obtained in Example 2. According to the result of the measurement, the peaks at 3.30 s (3), 7.31 s (1), and 8.77 s (1) ppm by the above-described $^1$H-NMR in deuterated methanol did not reveal a correlation with other peaks, also by the $^1$H-$^1$H COSY and NOESY measurement.

Accordingly, in the PQQ methanol adduct obtained in Example 2, it was found that a site to which methanol was added was the same as the expected structure.

When a site of addition to quinone is different, the methyl group is located adjacent to hydrogen on the ring of PQQ, and a correlation could be observed by the NOESY measurement.

When the PQQ ethanol adduct obtained in Example 5 was analyzed in the same manner, the chemical shifts (integral ratio) of $^1$H-NMR were 1.17 t (3), 3.60 q (2), 7.31 s (1), and 8.76 s (1). It was found that, from the result, one molecule of ethanol was added to the PQQ ethanol adduct obtained in Example 5.

Furthermore, the NOESY measurement was performed for structure determination of the PQQ ethanol adduct obtained in Example 5. According to the result of the measurement, a correlation between the peaks at 7.31 s (1) and 8.76 s (1) ppm on the aromatic ring and the peaks of the ethyl group at 1.17 t (3) and 3.60 q (2) ppm by the above-described $^1$H-NMR in deuterated methanol was not observed.

Accordingly, it was found that the PQQ ethanol adduct obtained in Example 5 had the same structure as the above-described structure of the PQQ methanol adduct obtained in Example 2.

2) Measurement in Deuterated Dimethyl Sulfoxide (Deuterated DMSO) Solvent

In a deuterated dimethyl sulfoxide (deuterated DMSO) solvent, $^1$H-NMR and $^{13}$C-NMR of the PQQ free body were measured. It is to be noted that, in the present example, the PQQ free body obtained by the same method as Example 1 was used for the PQQ free body.

According to the result of $^1$H-NMR of the PQQ free body, the chemical shifts (integral ratio) were 4.04 (4) broad, 7.19 d (1), and 8.59 s (1) ppm.

According to the result of $^{13}$C-NMR of the PQQ free body, there were peaks at 113.49, 124.42, 126.38, 127.56, 129.14, 134.33, 136.41, 146.75, 148.67, 160.87, 164.93, 168.60, 173.32, and 177.93 ppm.

In a deuterated dimethyl sulfoxide (deuterated DMSO) solvent, $^1$H-NMR and $^{13}$C-NMR of the PQQ methanol adduct obtained in Example 2 and the PQQ ethanol adduct obtained in Example 5 were measured.

A part derived from the PQQ structure had the same chemical shifts as the peaks of the above-described PQQ free body, by both of $^1$H-NMR and $^{13}$C-NMR.

In addition to the same chemical shifts as the above-described peaks of the PQQ free body, the PQQ methanol adduct obtained in Example 2 showed a peak at 3.15 ppm by $^1$H-NMR. The peak corresponded to the chemical shift of methanol. In addition, by $^{13}$C-NMR, a peak derived from the methyl group was observed at 48.66 ppm.

In the PQQ ethanol adduct obtained in Example 5, a part derived from the PQQ structure had the same chemical shifts as the above-described peaks of the PQQ free body, by both of $^1$H-NMR and $^{13}$C-NMR. Peaks derived from the ethyl group appeared at 1.04 t and 3.43 (q) by $^1$H-NMR, and 18.62 and 56.06 by $^{13}$C-NMR.

The result showed that the additional structure of the alcohol was broken in deuterated DMSO and returned to the original PQQ free body and the alcohol.

In deuterated DMSO, the $^1$H-$^1$H COSY and NOESY measurement of the PQQ methanol adduct obtained in Example 2 was performed. As is the case with the measurement in deuterated methanol, this did not reveal a correlation with other peaks.

3) IR (ATR) Analysis

Figure 2:
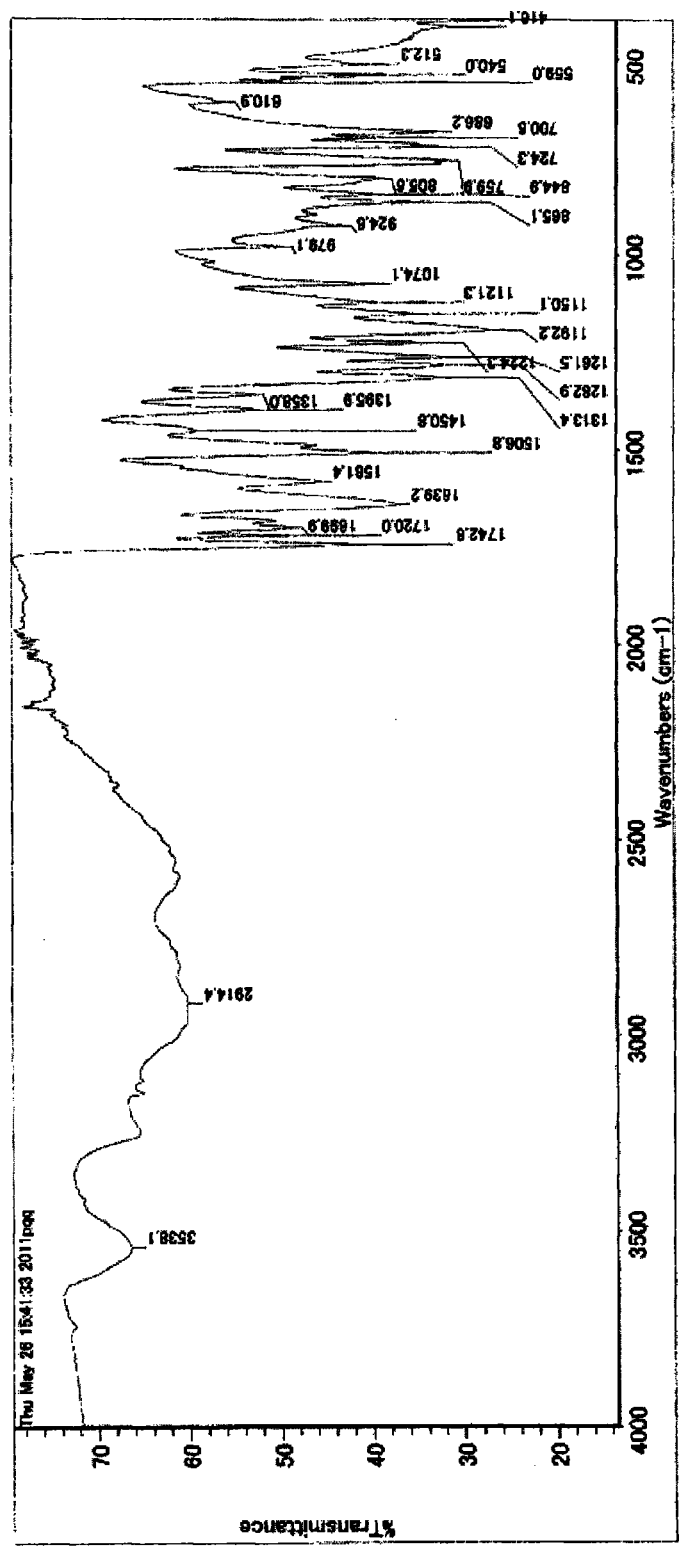
FIG. 2 is a diagram showing an IR result of a PQQ ethanol adduct.
Figure 3:
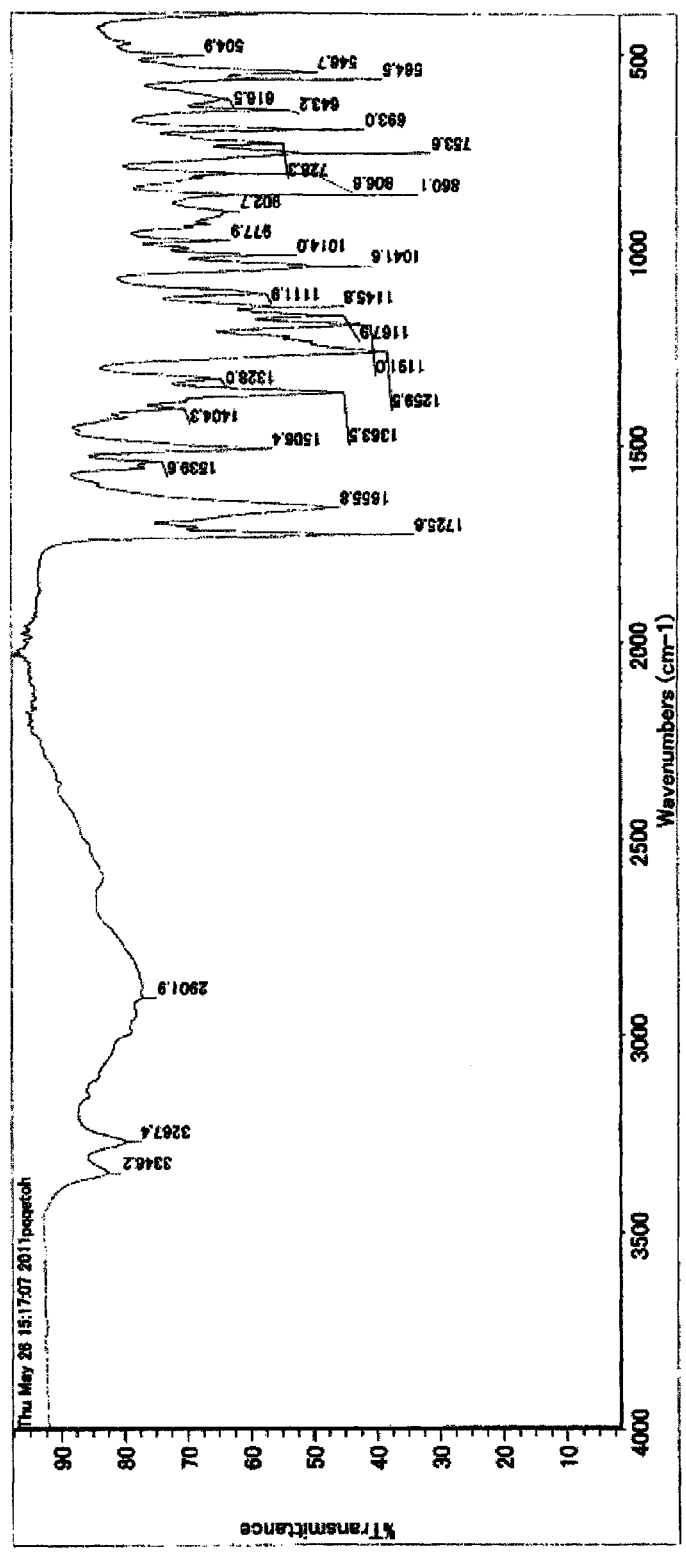
FIG. 3 is a diagram showing an IR result of a PQQ free body.
Figure 4:
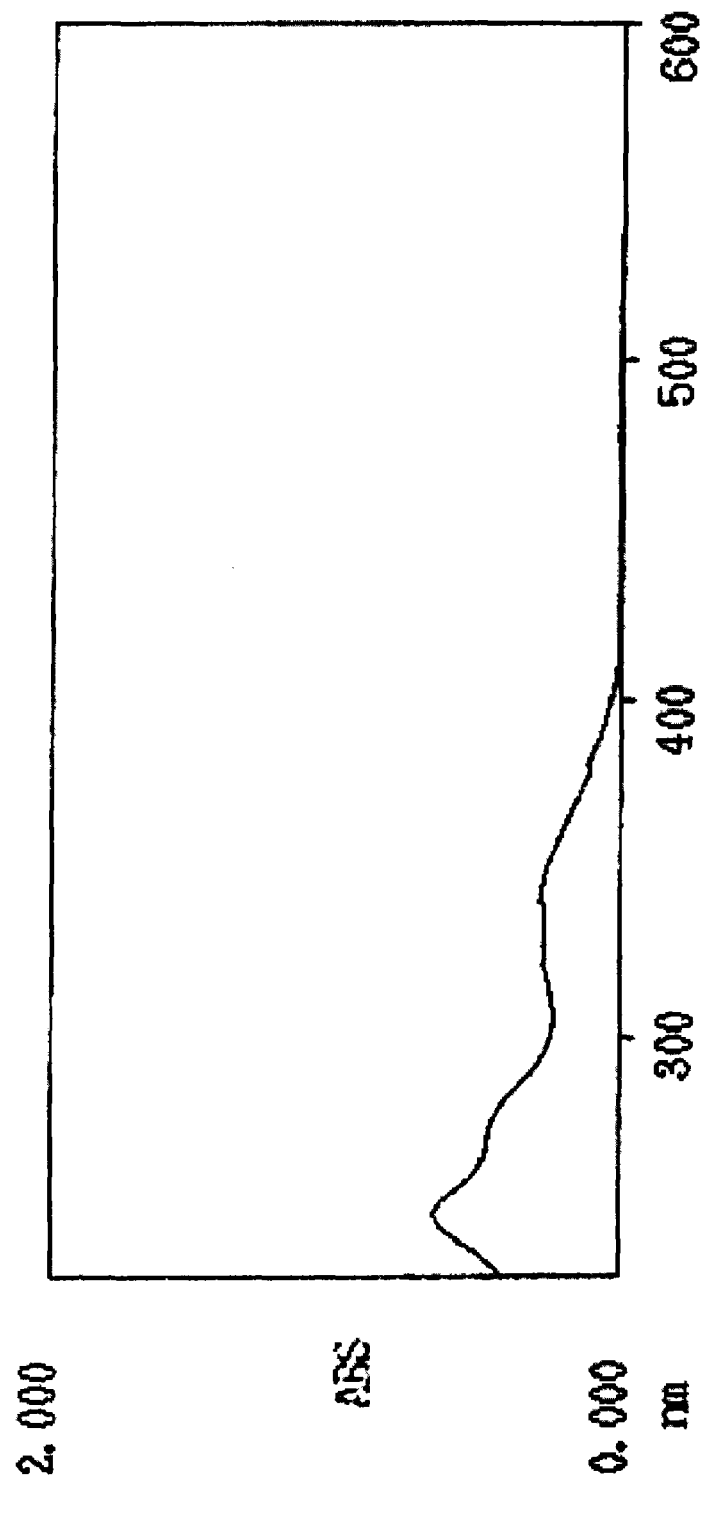
FIG. 4 is a diagram showing a DV spectrum result of a product obtained in Comparative Example 1.
Figure 5:
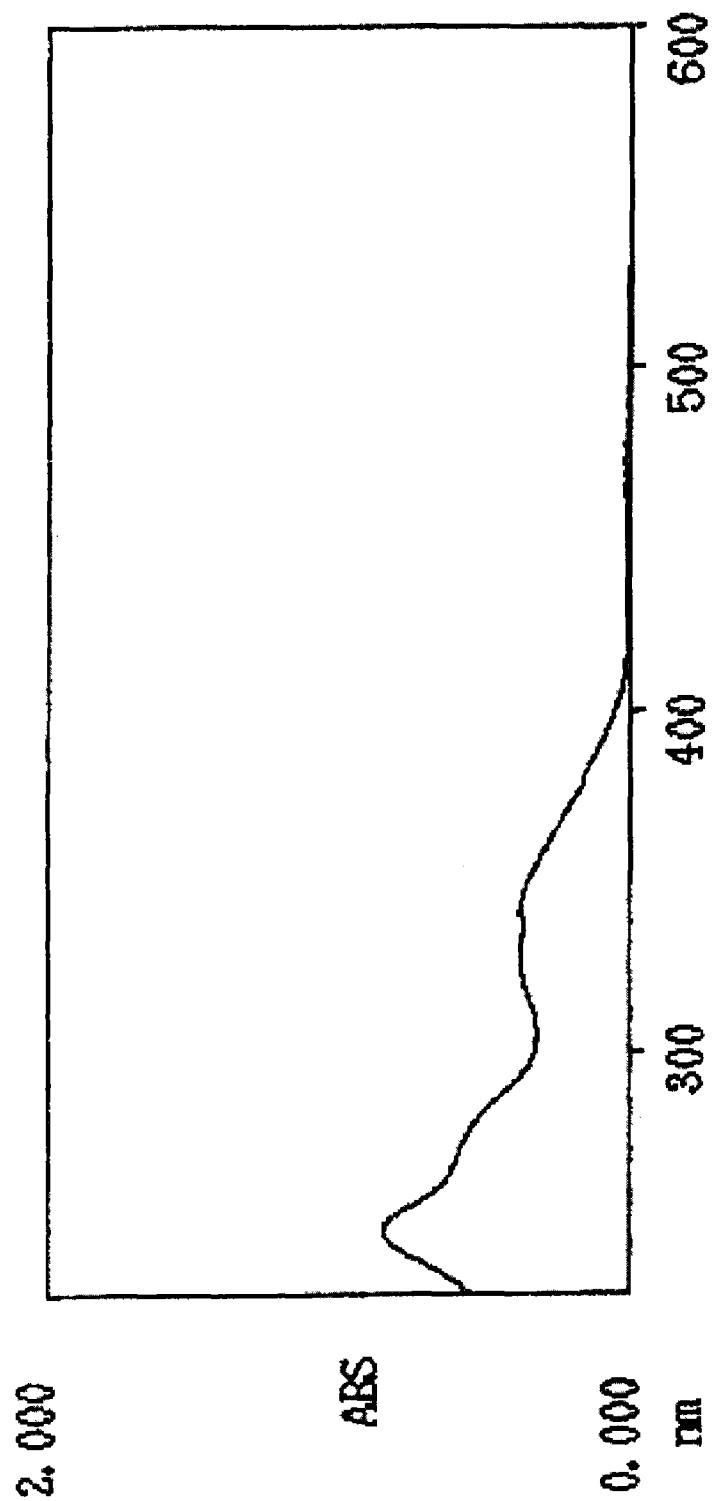
FIG. 5 is a diagram showing a DV spectrum result of a product obtained in Reference Example 1.
Figure 6:
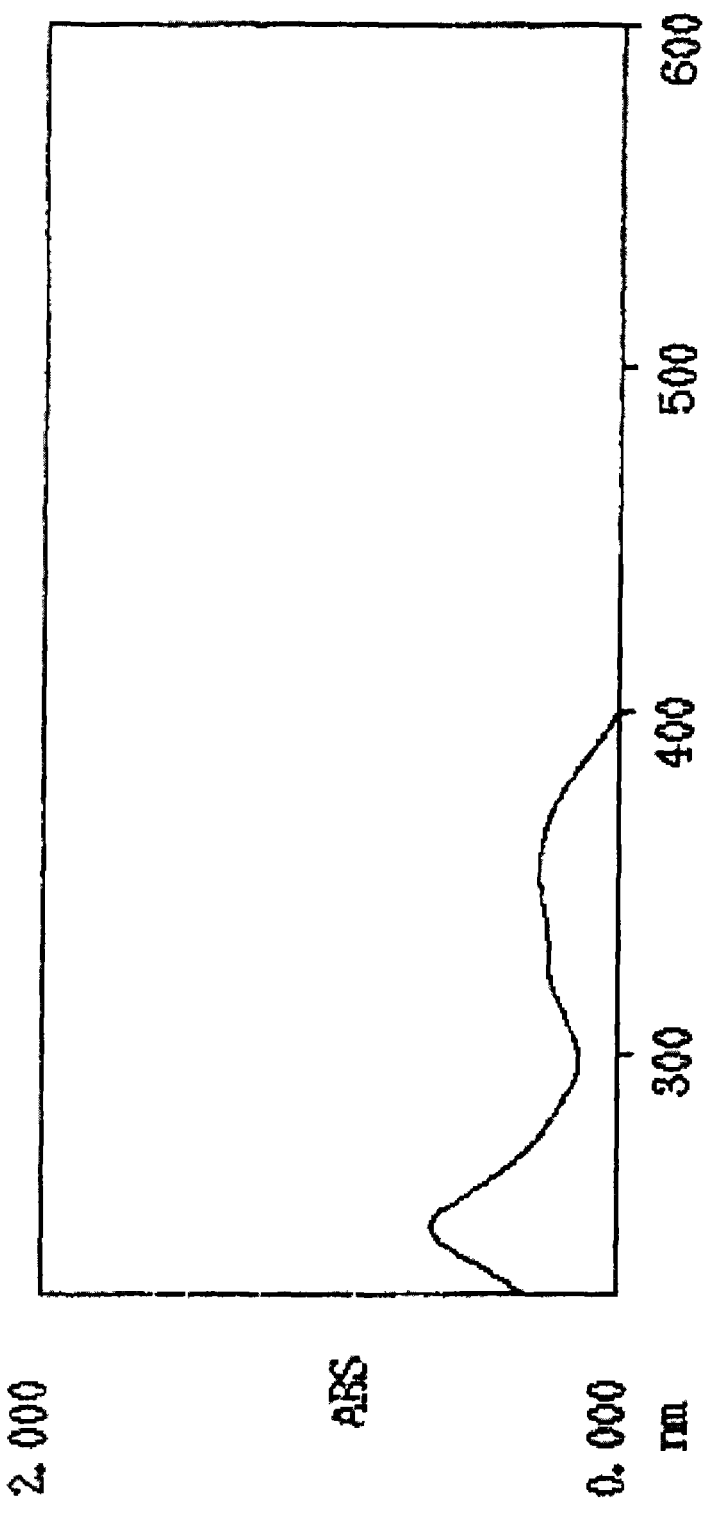
FIG. 6 is a diagram showing a UV spectrum result of a product obtained in Example 8-1.
Figure 7:
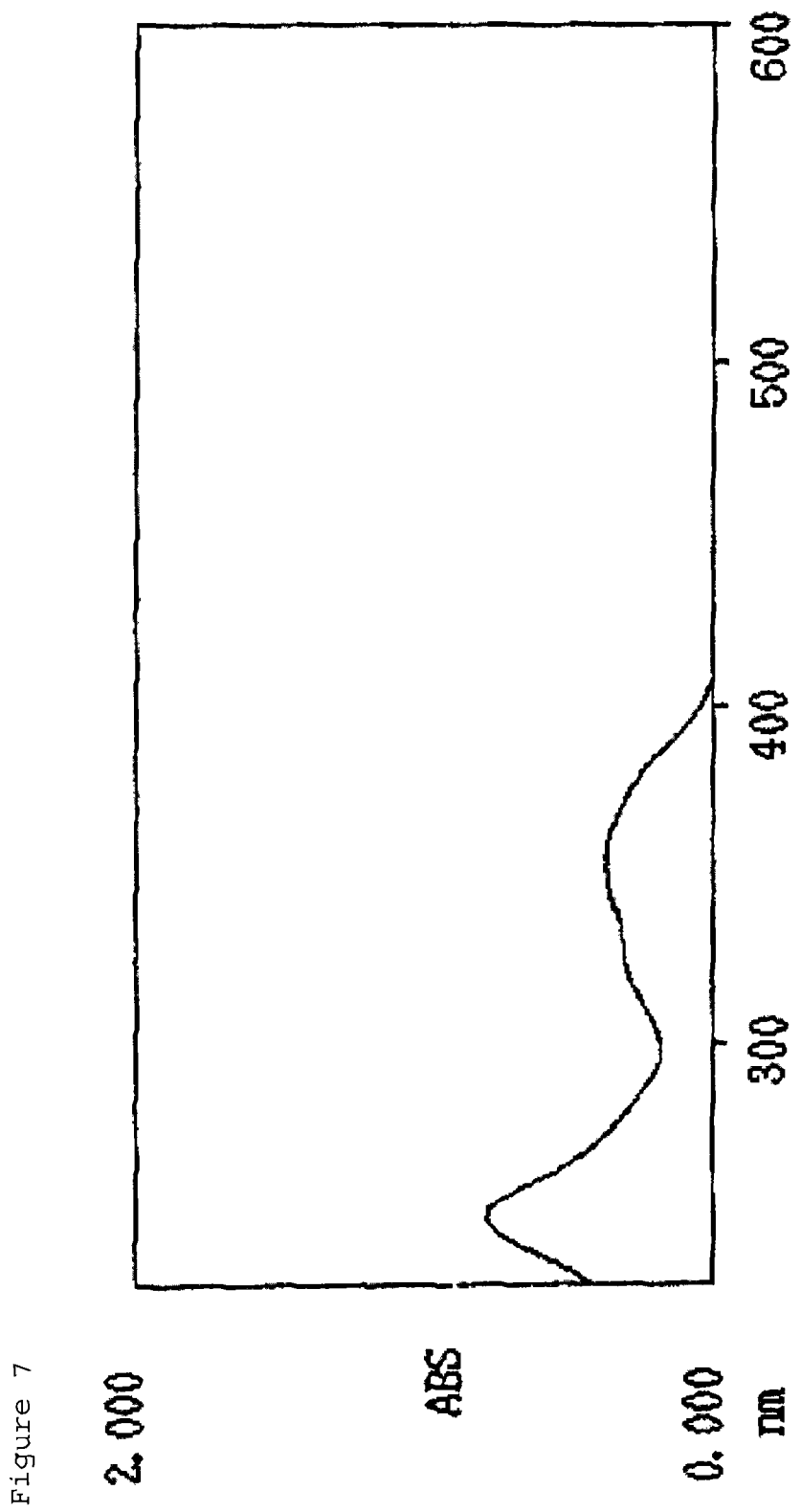
FIG. 7 is a diagram showing a UV spectrum result of a product obtained in Example 8-2.
Figure 8:
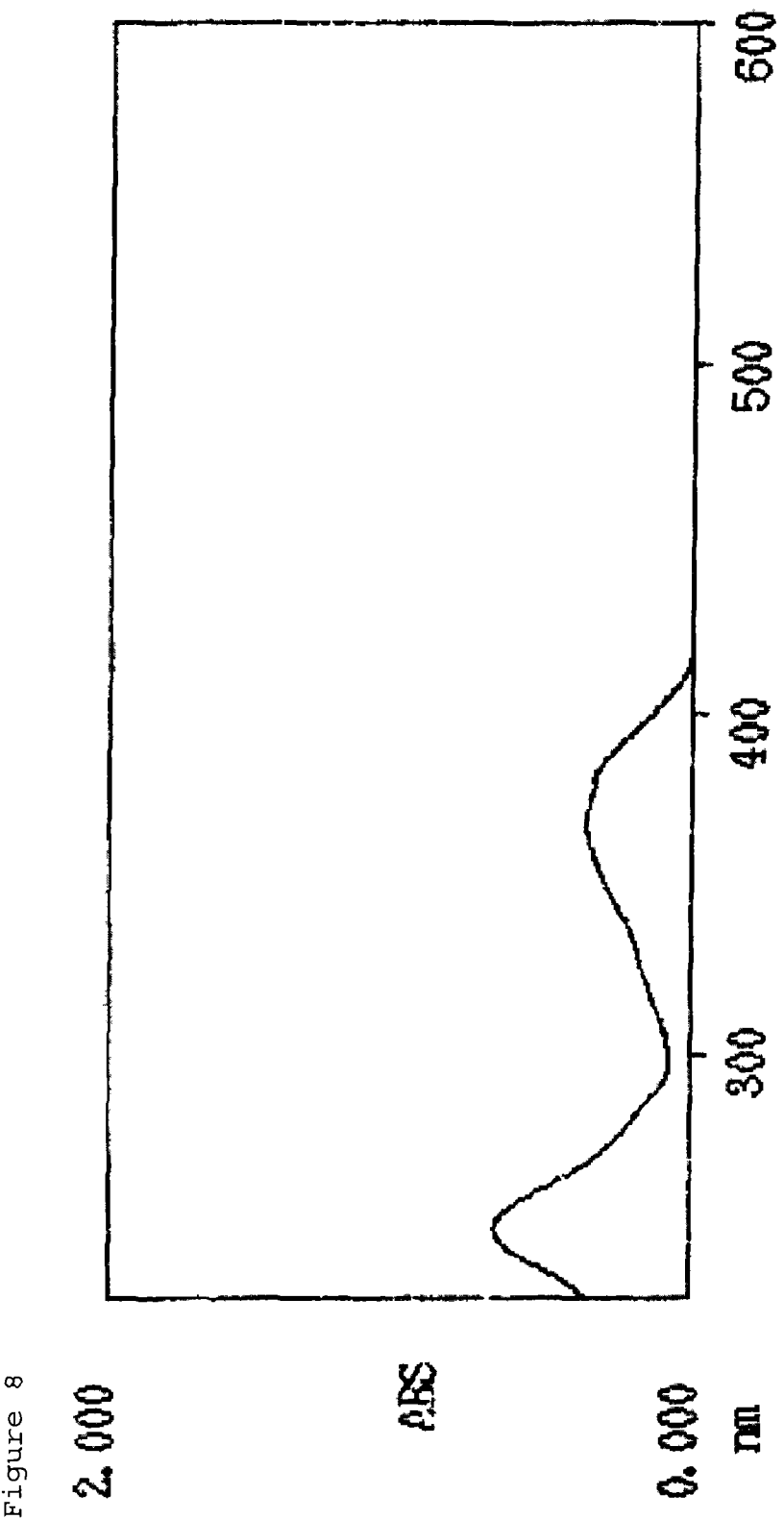
FIG. 8 is a diagram showing a UV spectrum result of a product obtained in Example 8-3.

The IR result of the PQQ methanol adduct obtained in Example 2, the IR result of the PQQ ethanol adduct obtained in Example 5, and the IR result of the PQQ free body are shown in FIGS. 1 to 3 in order.

The IR result of the PQQ methanol adduct obtained in Example 2 was almost the same as the IR result of the PQQ ethanol adduct obtained in Example 5. The peak at 3538 cm$^{-1}$ in the IR result of the PQQ ethanol adduct obtained in Example 5 was changed to the peak at 3260 cm$^{-1}$ and the peak at 3341 cm$^{-1}$ in the IR result of the PQQ methanol adduct obtained in Example 2.

Examples 8-1 to 8-3, Comparative Example 1, and Reference Example 1

UV Spectrum 10 mg of the PQQ free body was added to 10 mL of each of the following solvents to obtain a product. Moreover, the product was diluted 100 fold with the following predetermined solvent and the UV spectrum was measured.

The used solvents were as follows, respectively.

Comparative Example 1: water 100 mass %

Reference Example 1: water 90 mass %+methanol 10 mass %

Example 8-1: water 40 mass %+methanol 60 mass %

Example 8-2: water 10 mass %+methanol 90 mass %

Example 8-3: methanol 100 mass %

The UV spectrum results of the products obtained in Comparative Example 1, Reference Example 1, Example 8-1, Example 8-2, and Example 8-3 are shown in FIGS. 4 to 8 in order.

According to these UV spectrum results, it was found that a shoulder at 280 nm was disappearing as the methanol concentration of the used solvent was increased. Furthermore, it was found that the same spectrum was obtained by diluting first with methanol or water and the PQQ methanol adduct had rapid equilibrium.

It was found that the product when using the solvent of water 90 mass %+methanol 10 mass % as Reference Example 1 had almost the same spectrum as the product when using water as Comparative Example 1 and was not the hemiacetal structure but PQQ.

Examples 9 to 17

Reactivity with Various Alcohols and Stability

As shown in Table 1, 10 mg of the PQQ free body and 5 mL of each of various alcohols were mixed and reacted by heating at 65° C. In the reaction, time to dissolve the PQQ free body in each of the alcohols and change in color were observed. The results are shown in Table 1.

Furthermore, 10 μL of the obtained reaction liquid was added to 2 mL of water, the UV spectrum was measured, and whether or not it was the same as the spectrum of the PQQ free body was determined. The measurement was performed using the reaction liquids immediately after the completion of the reaction (0 hours), after 1 hour from the completion of the reaction, and after leaving at rest for 1 day at 30° C. The results are shown in Table 1.

TABLE 1

| Example | Reaction liquid Alcohol | Time to dissolve Color | UV spectrum (comparison with PQQ free body) | | |
|---|---|---|---|---|---|
| | | | 0 h | 1 h | 30° C. 1 day |
| 9 | Ethylene glycol | 2 h Yellow | Different | Different | Same |
| 10 | Propylene glycol | 2 h Yellow | Different | Different | Same |
| 11 | Polyethylene glycol 400 | 4 h Orange | Different | | Different |
| 12 | Dipropylene glycol | 4 h Orange | Same | | Same |
| 13 | Tripropylene glycol | 4 h Orange | Same | | Same |
| 14 | Glycerin | 12 h Yellow | Different | Different | — |
| 15 | Butoxyethanol | 4 h Orange | Same | | Same |
| 16 | 2-Methyl-1-propanol | 4 h Orange | Same | | Same |
| 17 | 1-Propanol | 4 h Yellow | Same | | Same |

According to the results in Table 1, in the case of using ethylene glycol and propylene glycol, these alcohols were easy to react with PQQ, and it was found that the obtained PQQ alcohol adducts stably existed in water for a few hours. Moreover, in the case of using polyethylene glycol, the obtained PQQ alcohol adduct was stable in water after the reaction. In the case of using glycerin, although glycerin was slow to react with PQQ, the obtained PQQ alcohol adduct was stable. In the case of using alcohols having only an alkyl group, although these alcohols were easy to react with PQQ, the obtained PQQ alcohol adducts immediately returned to PQQ free bodies.

According to the above results, it was found that properties of the PQQ alcohol adduct could be easily changed by selecting the kind of alcohol.

Examples 18 and 19, and Comparative Examples 2 and 3

Effect on Bacterial Growth

*Escherichia coli* JM109 was cultivated overnight in an LB medium at 30° C. The cultivated *Escherichia coli* JM109 was diluted with a phosphate buffer (PBS) having pH of 7.4 manufactured by GIBCO to obtain a solution 1 having turbidity at 660 nm of 0.57. To 8 mg of each sample shown in Table 2, 100 µL of the solution 1 was added at room temperature, and after 30 minutes, 900 µL of PBS was further added to obtain a solution 2. The solution 2 was planted in a petri dish with an LB agar medium and cultivated at 30° C., and a viable bacteria count was determined from the number of colonies in the solution 2.

TABLE 2

| | Sample | Viable bacteria count |
|---|---|---|
| Example 18 | PQQ methanol adduct | 0 |
| Example 19 | PQQ ethanol adduct | 0 |
| Comparative Example 2 | PQQ free body | 80 |
| Comparative Example 3 | Nothing | 5120000 |

PQQ methanol adduct: PQQ methanol adduct obtained in Example 2
PQQ ethanol adduct: PQQ ethanol adduct obtained in Example 5

It was found that the PQQ alcohol adduct of the present embodiment had an effect of suppressing bacteria growth and had a low risk of bacterial contamination while having functions equivalent to PQQ.

Examples 20 to 22, and Reference Examples 2 and 3

Reaction of PQQ disodium, Hydrochloric Acid, and Ethanol

As shown in Table 3, a predetermined amount of 2N hydrochloric acid was added to 1 mL of 0.2 M PQQ disodium water solution, and after the mixture was dried on a hot plate, it was reacted with 10 mL of ethanol at 50° C. for 1 hour and change in color was observed.

TABLE 3

| | HCl/PQQ disodium (molar ratio) | Color |
|---|---|---|
| Example 20 | 1 | Yellow |
| Example 21 | 2 | Orange |
| Example 22 | 5 | Orange |
| Reference Example 2 | 0 | Red |
| Reference Example 3 | 0.5 | Red |

When the amount of hydrochloric acid used was half of PQQ disodium, the reaction liquid remained in the red color. Moreover, when the amount of hydrochloric acid used was equimolar to PQQ disodium, the reaction liquid changed to the yellow color. Furthermore, when the amount of hydrochloric acid used was excessive compared to PQQ disodium, the reaction liquid changed to the orange color. According to these results, it was found that change in color of PQQ disodium (sodium structure) occurred by the addition of ethanol depending on the amount of hydrochloric acid used. Furthermore, it was found that, when using an alkali metal salt of PQQ as a raw material, an alcohol adduct could be formed by adding acid.

Examples 23 and 24, and Comparative Examples 4 to 6 Mixing with Coenzyme Q10

As shown in Table 4, coenzyme Q10 and each of various samples were mixed such that the weight ratio was 1:1, and the color of the obtained mixture was observed.

TABLE 4

| | Sample mixed with coenzyme Q10 | Color |
|---|---|---|
| Example 23 | PQQ methanol adduct | Yellow |
| Example 24 | PQQ ethanol adduct | Yellow |
| Comparative Example 4 | PQQ free body | Brown |
| Comparative Example 5 | PQQ disodium | Brown |
| Comparative Example 6 | Nothing | Yellow |

PQQ methanol adduct: PQQ methanol adduct obtained in Example 2
PQQ ethanol adduct: PQQ ethanol adduct obtained in Example 5

It was found that, the case where the alcohol adduct of the present embodiment was mixed with coenzyme Q10 was preferable because the change in color was small, compared with the case where the general PQQ free body or PQQ disodium was mixed with coenzyme Q10.

Example 25

2-Propanol adduct 0.86 g of the PQQ free body and 80 g of 2-propanol were mixed to be reacted for 24 hours while carrying out heating reflux. Isopropanol was removed from the obtained reaction liquid by an evaporator to obtain 1.06 g of a yellow solid (PQQ 2-propanol adduct).

When performing the $^1$H-NMR measurement of the obtained yellow solid in deuterated methanol, peaks were shown at 1.15, 3.92, 7.27, and 8.66 ppm, and it was found that one molecule of isopropanol was added.

In addition, by performing the LC analysis of the obtained yellow solid, all were detected as PQQ.

Example 26-1

Figure 9:
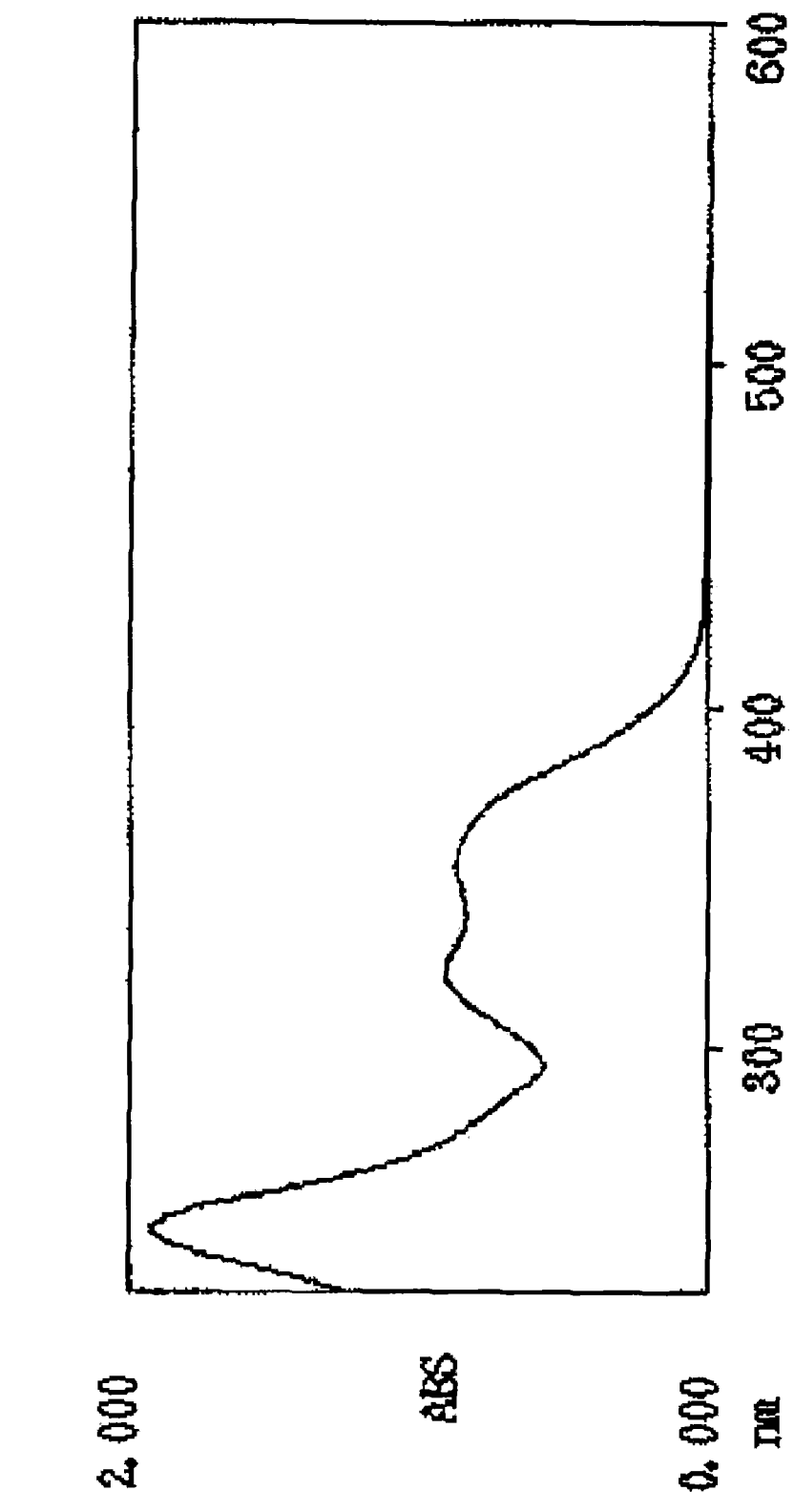
FIG. 9 is a diagram showing a UV spectrum result of a 100% methanol solution obtained in Example 26-1.

PQQ Disodium 10 mg of PQQ disodium was added to 10 mL of methanol to form a suspension. A solution obtained by diluting the suspension 20 fold with methanol (100% methanol solution) was manufactured. The UV spectrum of the solution was measured. The result is shown in FIG. 9.

Example 26-2

Figure 10:
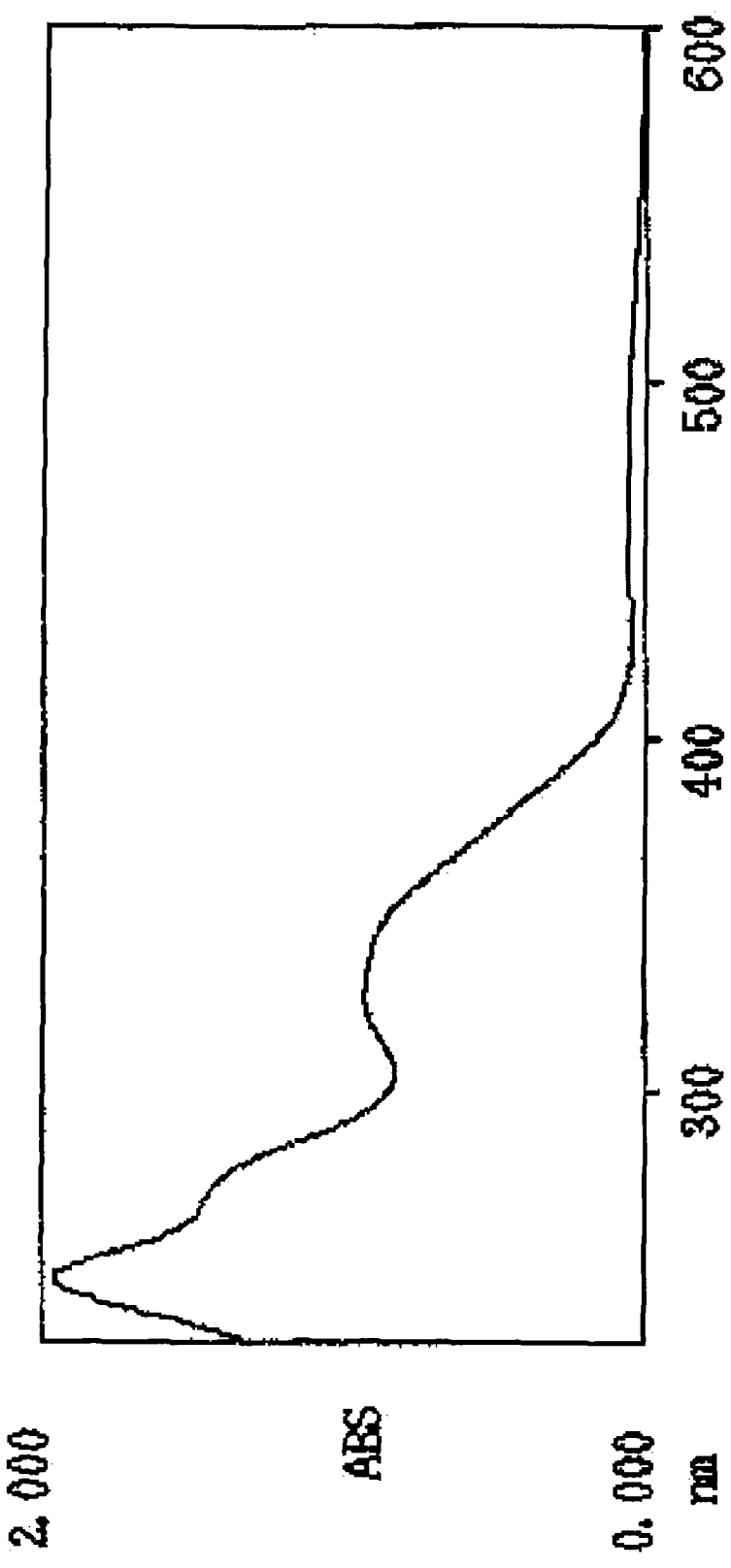
FIG. 10 is a diagram showing a UV spectrum result of a 5% methanol solution obtained in Example 26-2.
Figure 11:
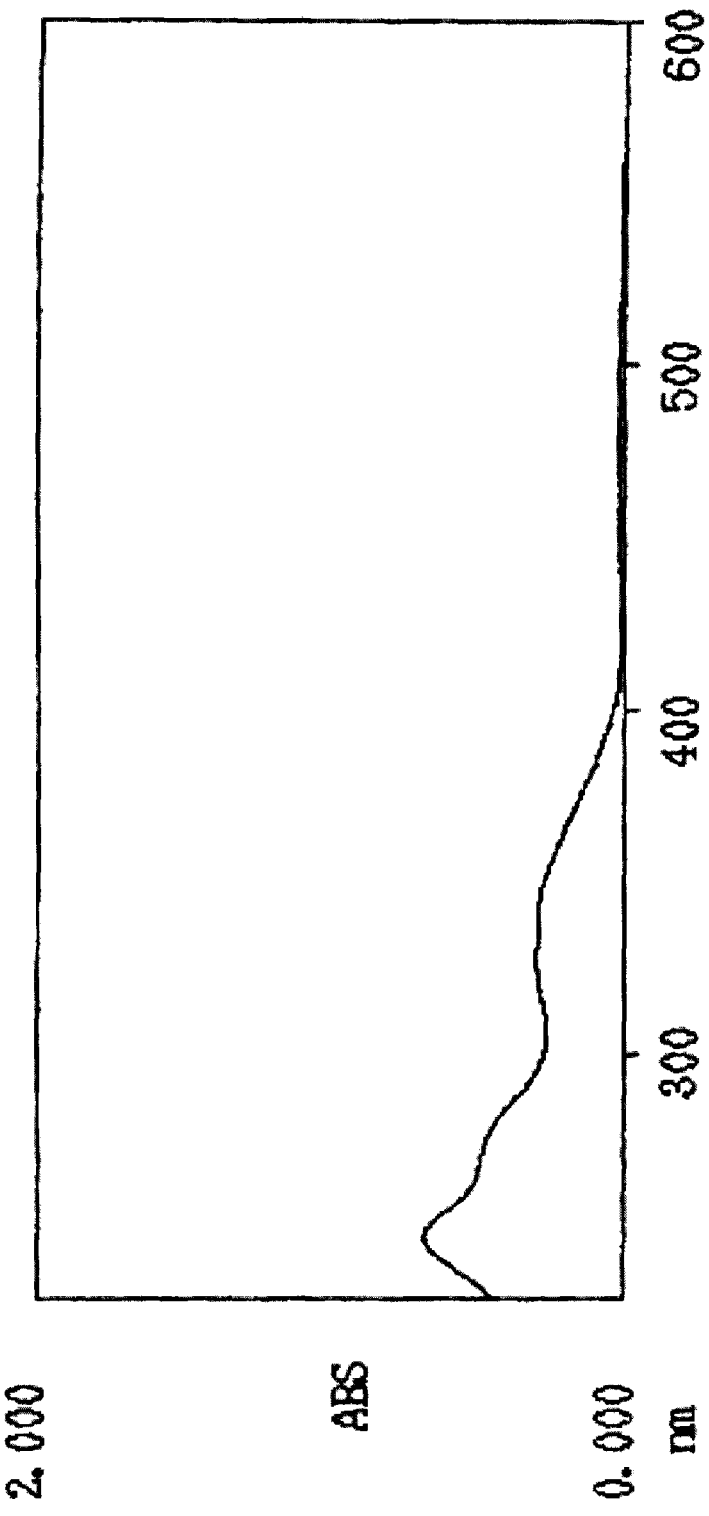
FIG. 11 is a diagram showing a UV spectrum result of a product obtained in Comparative Example 7.
Figure 12:
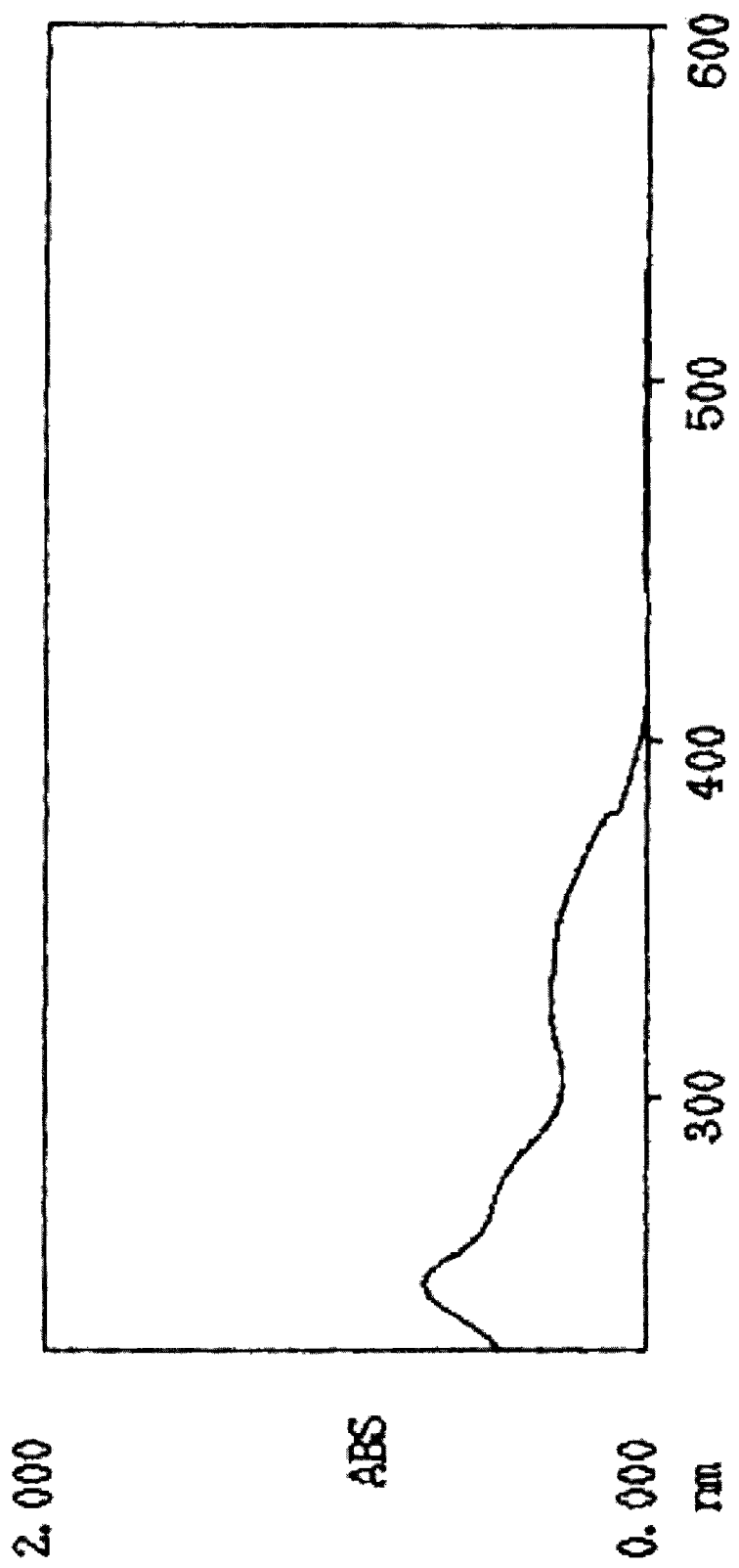
FIG. 12 is a diagram showing a UV spectrum result of a product obtained in Reference Example 4.
Figure 13:
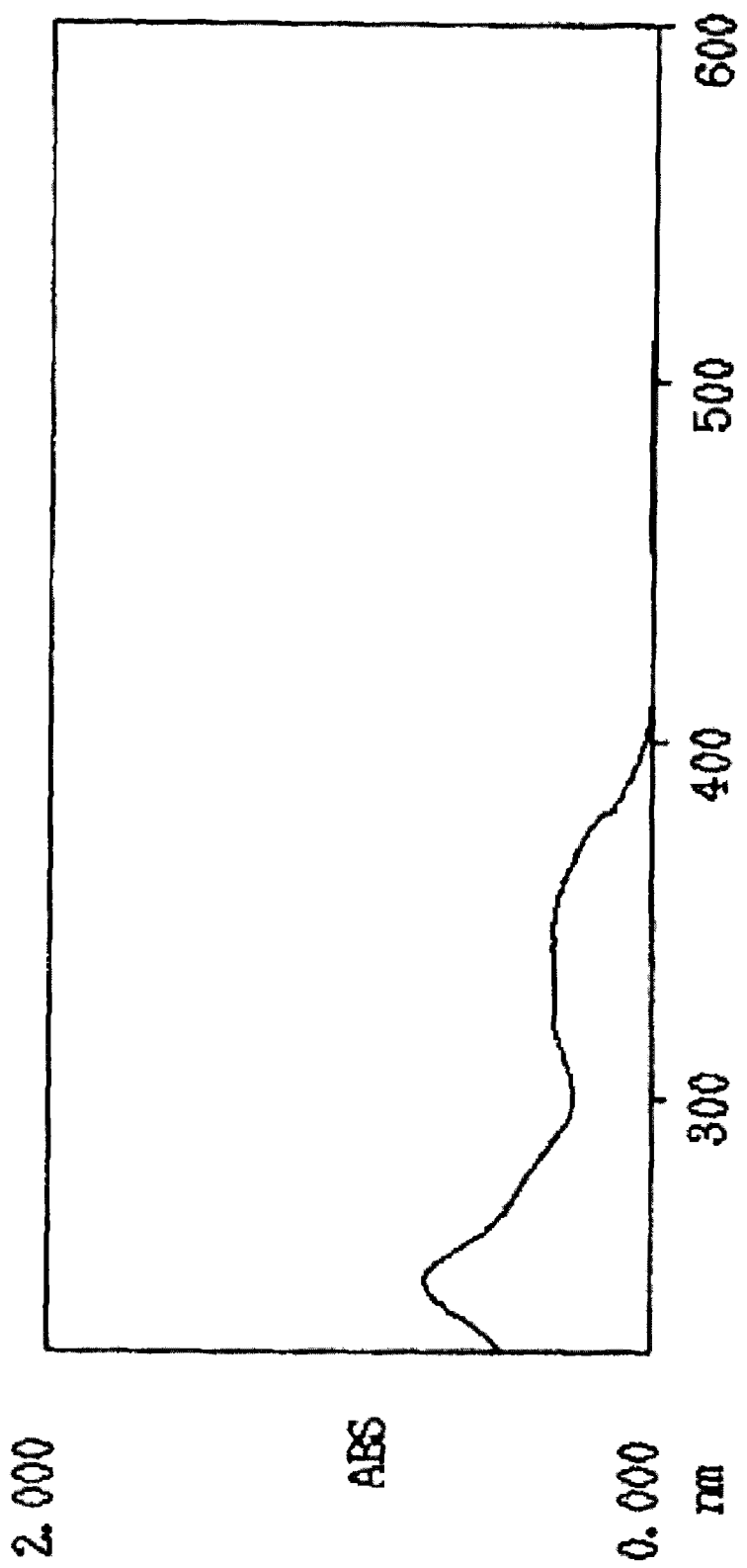
FIG. 13 is a diagram showing a UV spectrum result of a product obtained in Example 27-1.
Figure 14:
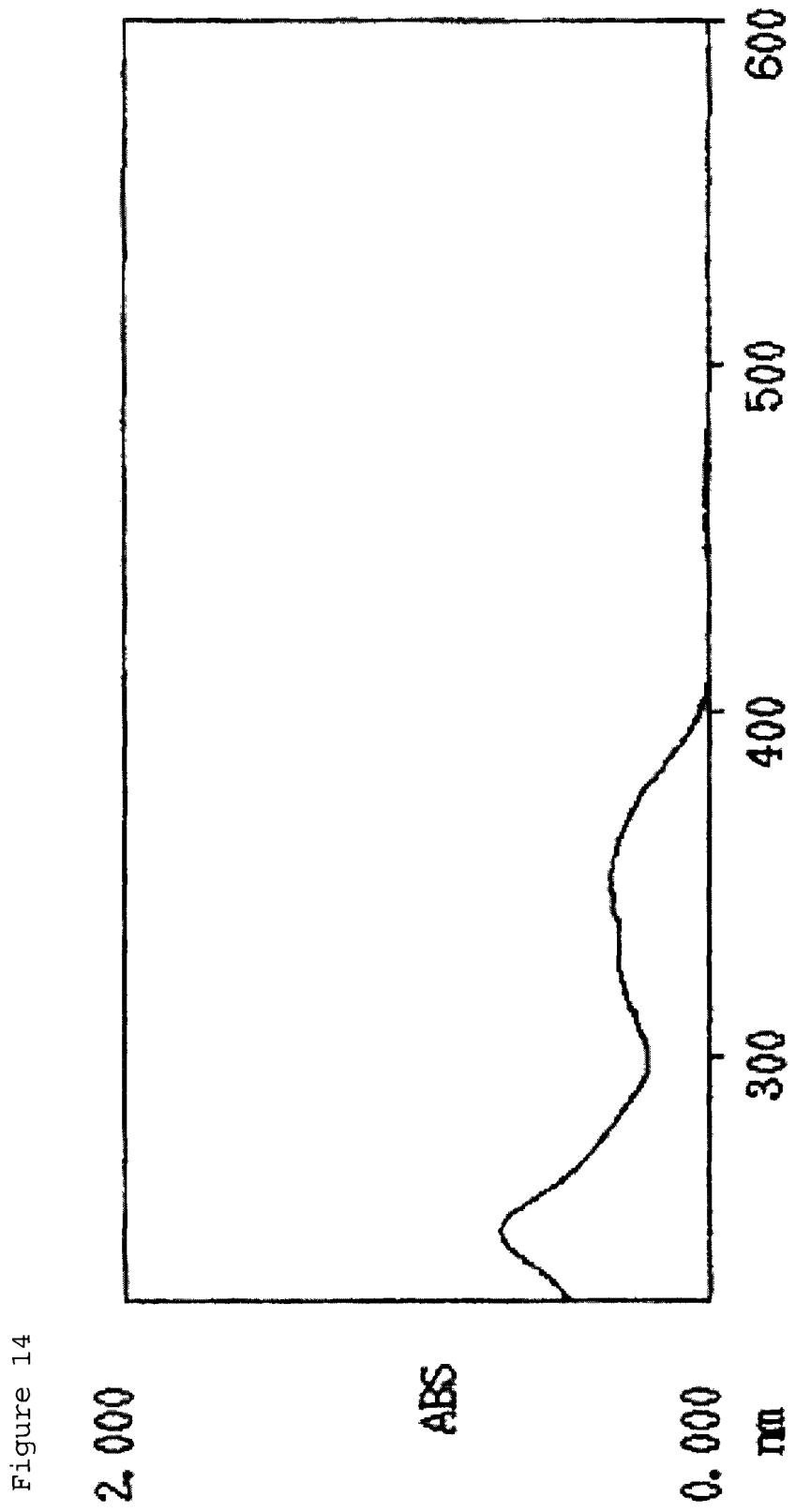
FIG. 14 is a diagram showing a UV spectrum result of a product obtained in Example 27-2.
Figure 15:
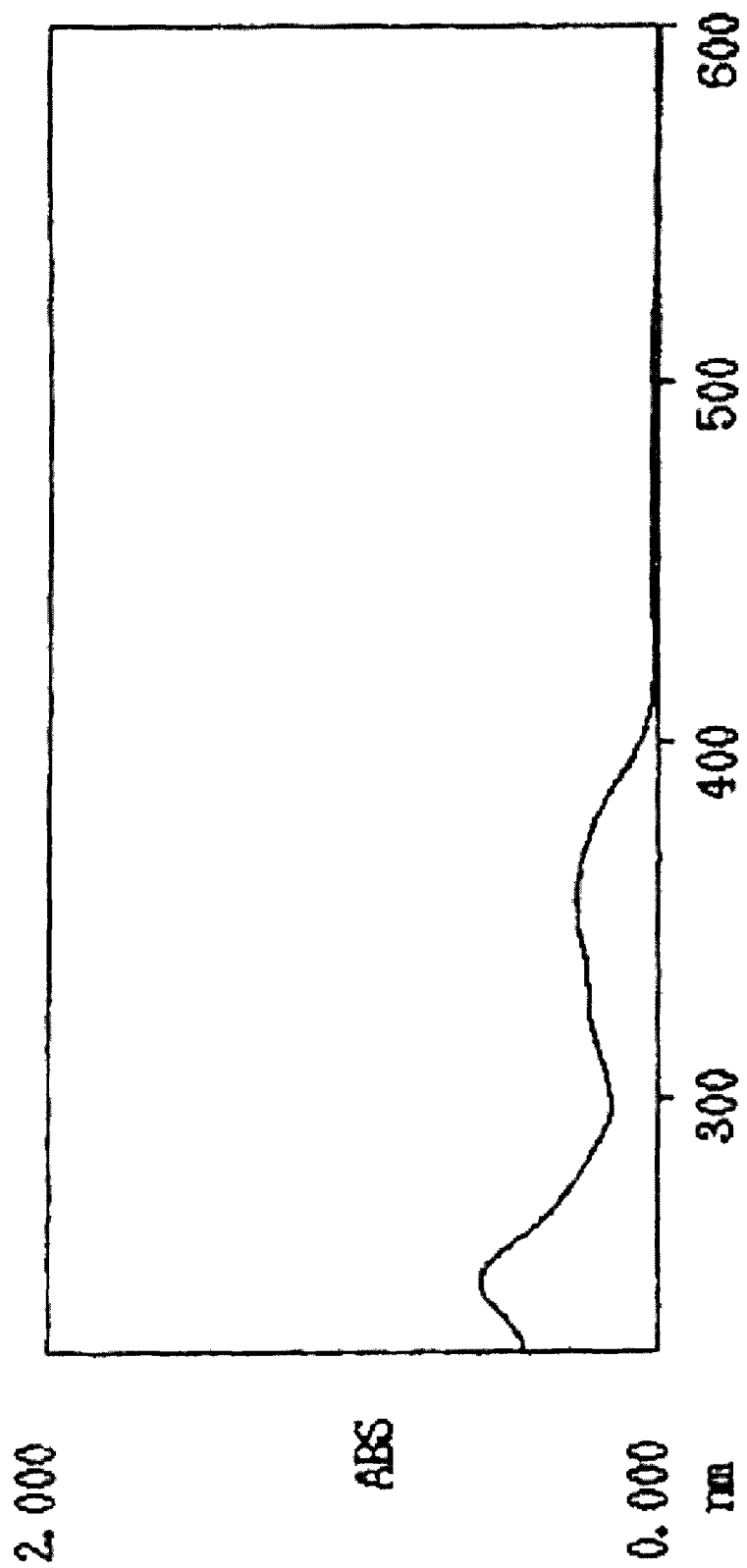
FIG. 15 is a diagram showing a UV spectrum result of a product obtained in Example 27-3.

PQQ Disodium 10 mg of PQQ disodium was added to 10 mL of methanol to form a suspension. A solution obtained by diluting the suspension 20 fold with water (5% methanol solution) was manufactured. The UV spectrum of the solution was measured. The result is shown in FIG. 10.

In the UV spectra of Example 26-1 and Example 26-2, the 100% methanol solution had peaks at 250, 320, and 350 nm, and the 5% methanol solution had peaks at 250, 280 (shoulder), and 330 nm. According to these results, it was found that a shoulder disappeared in the 100% methanol solution. That is, it was found that, when PQQ disodium was used as a raw material, the same reactivity as the PQQ free body was shown and the PQQ methanol adduct is generated.

Examples 27-1 to 27-3, Comparative Example 7, and Reference Example 4

UV Spectrum 10 mg of the PQQ free body was added to 10 mL of each of the following solvents to obtain a product. Moreover, the product was diluted 100 fold with the following predetermined solvent and the UV spectrum was measured.

The used solvents were as follows, respectively.

Comparative Example 7: water 100 mass %

Reference Example 4: water 90 mass %+ethanol 10 mass %

Example 27-1: water 40 mass %+ethanol 60 mass %

Example 27-2: water 10 mass %+ethanol 90 mass %

Example 27-3: ethanol 100 mass %

The UV spectrum results of the products obtained in Comparative Example 7, Reference Example 4, Example 27-1, Example 27-2, and Example 27-3 are shown in FIGS. 11 to 15 in order.

Examples 28-1 to 28-8

Stability Test

As shown in Table 5, 5 mg of each sample was charged in a 0.25 mL polypropylene container, the container was put in an oven, and change at each temperature was observed after 0.5, 3, and 24 hours and 7 days. It is to be noted that 100 μL of ODO, Nisshin Oillio was used as an edible fat and oil.

TABLE 5

| | Each sample, State of container | Observation result after 0.5 to 24 hours | Observation result after 7 days |
|---|---|---|---|
| Example 28-1 | PQQ ethanol adduct, 30° C. Container's cover closed | Yellow powder after 24 hours, Without change | Without change |
| Example 28-2 | PQQ ethanol adduct, 30° C. Container's cover opened | Yellow powder after 3 hours. Reddened a little after 24 hours. | Discolored to red |
| Example 28-3 | PQQ ethanol adduct + edible fat and oil, 70° C. Container's cover opened | Yellow powder suspension after 24 hours, Without change | Without change |
| Example 28-4 | PQQ ethanol adduct, 70° C. Container's cover closed | Yellow powder after 24 hours, Without change | Without change |
| Example 28-5 | PQQ methanol adduct, 30° C. Container's cover closed | Yellow powder after 24 hours, Without change | Without change |
| Example 28-6 | PQQ methanol adduct, 30° C. Container's cover opened | Discolored to red after 0.5 hours. Red powder after 24 hours. | Red powder |
| Example 28-7 | PQQ methanol adduct + edible fat and oil, 70° C. Container's cover opened | Yellow powder suspension after 24 hours, Without change | Red powder suspension |
| Example 28-8 | PQQ methanol adduct, 70° C. Container's cover closed | Yellow powder after 24 hours, Without change | Without change |

PQQ methanol adduct: PQQ methanol adduct obtained in Example 2
PQQ ethanol adduct: PQQ ethanol adduct obtained in Example 5

According to the results in Table 5, it was found that the PQQ methanol adduct was stable in the sealed state of the container, but was immediately discolored to red in the opened state in which the container's cover was opened. It is considered that this is because the added methanol was desorbed and the PQQ methanol adduct returned to PQQ. On the other hand, it was found that the PQQ ethanol adduct was more stable than the PQQ methanol adduct and was not discolored immediately even if the container was in the opened state. According to these results, it was found that the PQQ ethanol adduct was easy to be handled and was more preferable.

Furthermore, by mixing an edible fat and oil, discoloration of the PQQ alcohol adduct did not proceed even if the container was in the opened state at a high temperature. According to the result, it was found that an edible fat and oil was effective in stabilizing the PQQ alcohol adduct of the present embodiment.

INDUSTRIAL APPLICABILITY

The present invention can be widely used as medical drugs or quasi drugs, foods, functional foods, and feeding stuffs for humans or for animals.

The invention claimed is:
1. A composition comprising:
(a) a compound represented by formula (A) or (B), or a salt thereof:

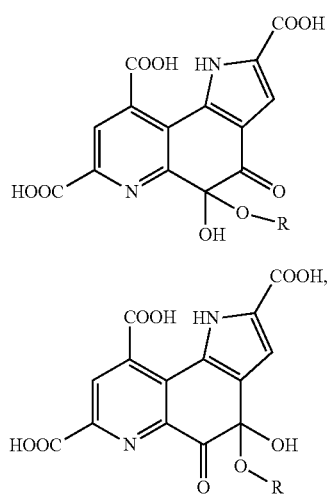

where R is alkyl, hydroxyalkyl, dihydroxyalkyl, or alkoxylalkyl; and
(b) coenzyme Q10.
2. A beverage, comprising the composition of claim 1.
3. A food, comprising the composition of claim 1.
4. A cosmetic, comprising the composition of claim 1.
5. The composition according to claim 1, wherein the composition is in a form of a powder, a tablet, a chewable tablet, a capsule, a granule, an injectable, a liquid, an eye drop, a lotion, a hair tonic, a cosmetic emulsion, a spray liquid, an aerosol, a drink liquid, a liquid fertilizer, or a preservation solution.
6. A method for manufacturing the composition according to claim 1, the method comprising:
(a) adding one equivalent of an alcohol represented by formula (2) to the pyrroloquinoline quinone represented by formula (1) or a salt thereof:

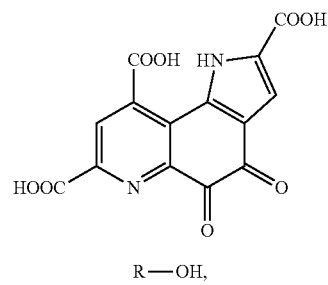

wherein where R is alkyl, hydroxyalkyl, dihydroxyalkyl, or alkoxylalkyl; and
(b) admixing coenzyme Q10 with the compound obtained by step (a).

7. The method according to claim 6, wherein said adding is performed in a solvent having a water content of 50 mass % or less.
8. The method according to claim 6, comprising adding the alcohol represented by formula (2) to a monoalkali metal salt of the pyrroloquinoline quinone.
9. The method according to claim 7, comprising adding the alcohol represented by formula (2) to a monoalkali metal salt of the pyrroloquinoline quinone.
10. A compound by formula (A) or (B), or a salt thereof:

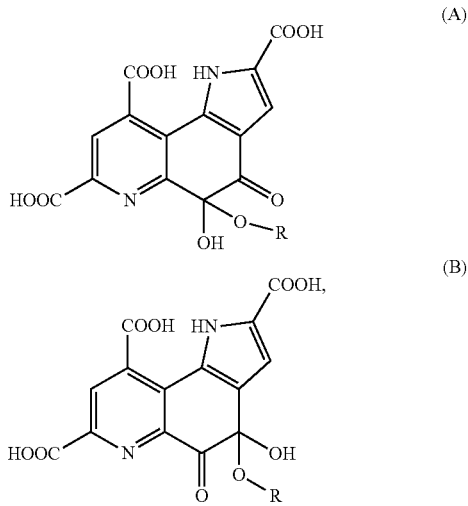

where R is hydroxyalkyl, dihydroxyalkyl, or alkoxylalkyl.
11. A composition, comprising the compound or the salt thereof of claim 10.
12. The composition according to claim 11, wherein the composition is selected from a beverage, a food or a cosmetic.
13. The composition according to claim 11, comprising coenzyme Q10.
14. The composition according to claim 13, wherein the composition is in a form of a powder, a tablet, a chewable tablet, a capsule, a granule, an injectable, a liquid, an eye drop, a lotion, a hair tonic, a cosmetic emulsion, a spray liquid, an aerosol, a drink liquid, a liquid fertilizer, or a preservation solution.
15. The composition according to claim 13, wherein the composition is selected from a beverage, a food or a cosmetic.
16. A method for manufacturing the compound or the salt thereof according to claim 10, the method comprising:
adding one equivalent of an alcohol represented by formula (2) to the pyrroloquinoline quinone represented by formula (1) or a salt thereof:

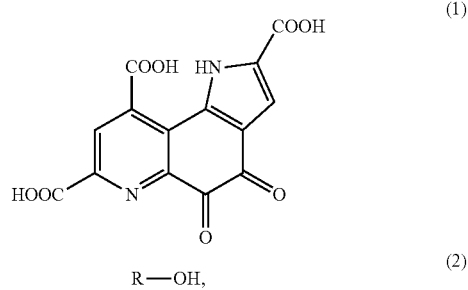

wherein R is hydroxyalkyl, dihydroxyalkyl, or alkoxylalkyl.

17. The method according to claim 16, wherein said adding is performed in a solvent having a water content of 50 mass % or less.

18. The method according to claim 16, comprising adding the alcohol represented by formula (2) to a monoalkali metal salt of the pyrroloquinoline quinone.

19. The method according to claim 16, further comprising admixing coenzyme Q10 to the compound thus obtained.

* * * * *